US012364692B2

(12) United States Patent
Shudo et al.

(10) Patent No.: US 12,364,692 B2
(45) Date of Patent: Jul. 22, 2025

(54) TOPICAL NALOXONE COMPOSITIONS AND METHODS FOR USING THE SAME

(71) Applicant: Teikoku Pharma USA, Inc., San Jose, CA (US)

(72) Inventors: Jutaro Shudo, San Jose, CA (US); Jianye Wen, San Jose, CA (US); Russell Haynes, San Jose, CA (US); Asha Sunkara, San Jose, CA (US); Bret Berner, San Jose, CA (US)

(73) Assignee: Teikoku Pharma USA, Inc., San Jose, CA (US)

( * ) Notice: Subject to any disclaimer, the term of this patent is extended or adjusted under 35 U.S.C. 154(b) by 275 days.

(21) Appl. No.: 17/791,134

(22) PCT Filed: Feb. 11, 2021

(86) PCT No.: PCT/US2021/017550
§ 371 (c)(1),
(2) Date: Jul. 6, 2022

(87) PCT Pub. No.: WO2021/163252
PCT Pub. Date: Aug. 19, 2021

(65) Prior Publication Data
US 2023/0065128 A1 Mar. 2, 2023

Related U.S. Application Data

(60) Provisional application No. 62/976,967, filed on Feb. 14, 2020.

(51) Int. Cl.
*A61P 17/04* (2006.01)
*A61K 9/00* (2006.01)
*A61K 9/06* (2006.01)
*A61K 9/14* (2006.01)
*A61K 31/485* (2006.01)
*A61K 47/10* (2017.01)
*A61K 47/12* (2006.01)
*A61K 47/14* (2017.01)
*A61K 47/22* (2006.01)

(52) U.S. Cl.
CPC .......... *A61K 31/485* (2013.01); *A61K 9/0014* (2013.01); *A61K 9/06* (2013.01); *A61K 47/10* (2013.01); *A61K 47/12* (2013.01); *A61K 47/14* (2013.01); *A61K 47/22* (2013.01); *A61P 17/04* (2018.01)

(58) Field of Classification Search
CPC ...... A61K 31/485; A61K 9/0014; A61K 9/06; A61K 47/10; A61K 47/12; A61K 47/14; A61K 47/22; A61P 17/04
See application file for complete search history.

(56) References Cited

U.S. PATENT DOCUMENTS

| | | |
|---|---|---|
| 4,416,886 A | 11/1983 | Bernstein |
| 4,573,995 A | 3/1986 | Chen et al. |
| 4,626,539 A | 12/1986 | Aungst et al. |
| 5,096,715 A | 3/1992 | Sinclair |
| 5,595,735 A * | 1/1997 | Saferstein .............. A61K 47/10 424/94.64 |
| 5,958,379 A | 9/1999 | Regenold et al. |
| 5,985,317 A | 11/1999 | Venkateshwaran et al. |
| 6,093,419 A | 7/2000 | Rolf |
| 6,365,178 B1 | 4/2002 | Venkateshwaran et al. |
| 6,500,838 B2 | 12/2002 | Shuster et al. |
| 6,569,449 B1 | 5/2003 | Stinchcomb et al. |
| 7,879,870 B2 | 2/2011 | Smith et al. |
| 7,910,599 B2 | 3/2011 | Sinclair |
| 8,314,118 B2 | 11/2012 | Zagon et al. |
| 8,685,381 B2 | 4/2014 | Schlessinger et al. |
| 9,551,996 B2 | 1/2017 | Baumgartner et al. |
| 9,895,384 B1* | 2/2018 | Kydonieus ............... C07F 7/00 |
| 2003/0003113 A1 | 1/2003 | Lewandowski |
| 2003/0017119 A1* | 1/2003 | Rabinowitz .......... A61K 31/501 424/46 |
| 2004/0116528 A1* | 6/2004 | Haas .................... A61K 9/0019 514/569 |
| 2004/0126323 A1 | 7/2004 | Shevchuk et al. |

(Continued)

FOREIGN PATENT DOCUMENTS

| | | |
|---|---|---|
| CA | 1189794 A | 7/1985 |
| CA | 3130619 C | 8/2022 |

(Continued)

OTHER PUBLICATIONS

Panchagnula et al., "Transdermal delivery of naloxone: skin permeation, pharmacokinetic, irritancy and stability studies," International Journal of Pharmaceutics 293 (2005) 213-223 (Year: 2005).*
Kumar et al., "Removal of Peroxides in Polyethylene Glycols by Vacuum Drying: Implications in the Stability of Biotech and Pharmaceutical Formulations," AAPS PharmSci Tech 2006; 7 (3). (Year: 2006).*
PCT International Search Report and Written Opinion, PCT Application No. PCT/US21/17550, Apr. 27, 2021, 11 pages.
European Patent Office, Extended European Search Report, European Patent Application No. 21754221.6, Feb. 7, 2024, 11 pages.
Liu, W. "'13$^{th}$ 5-Year' Planning Textbook of National Chinese Medicine Industry Higher Education, Polymer Material Science in Pharmaceuticals." China Press of Traditional Chinese Medicine, Jul. 2017, pp. 153.

(Continued)

*Primary Examiner* — Jared Barsky
(74) *Attorney, Agent, or Firm* — Miho Kaneko; Carl Morales; Goodwin Procter LLP

(57) ABSTRACT

Aspects of the invention include topical naloxone compositions for locally delivering naloxone to the skin of a subject. Topical compositions according to certain embodiments are storage stable non-aqueous topical compositions that include naloxone free base and a non-aqueous vehicle, wherein the compositions are substantially free of naloxone N-oxide. Also provided are methods of using the topical compositions to locally deliver naloxone to a subject, as well as kits containing the topical naloxone compositions.

17 Claims, 9 Drawing Sheets

(56) References Cited

U.S. PATENT DOCUMENTS

| | | |
|---|---|---|
| 2004/0191301 A1 | 9/2004 | Van Duren |
| 2005/0054991 A1 | 3/2005 | Tobyn et al. |
| 2005/0142176 A1 | 6/2005 | Wang et al. |
| 2006/0078603 A1 | 4/2006 | Nguyen |
| 2009/0041687 A1 | 2/2009 | Beumer et al. |
| 2009/0130178 A1 | 5/2009 | Oronsky et al. |
| 2011/0082167 A1 | 4/2011 | Pisak et al. |
| 2011/0244022 A1 | 10/2011 | Cottrell et al. |
| 2011/0245278 A1 | 10/2011 | Pisak et al. |
| 2012/0252831 A1 | 10/2012 | Pisak et al. |
| 2012/0277695 A1 | 11/2012 | Cottrell et al. |
| 2013/0101660 A1 | 4/2013 | Cottrell et al. |
| 2015/0005337 A1 | 1/2015 | Carrara et al. |
| 2015/0098983 A1 | 4/2015 | Pongpeerapat et al. |
| 2015/0352100 A1 | 12/2015 | Bigliardi et al. |
| 2016/0256451 A1 | 9/2016 | Rey et al. |
| 2016/0256452 A1 | 9/2016 | Rey et al. |
| 2016/0279124 A1 | 9/2016 | Markel et al. |
| 2017/0143698 A1 | 5/2017 | Talton |
| 2017/0189393 A1 | 7/2017 | Bear et al. |
| 2017/0342084 A1* | 11/2017 | McCarthy .......... A61P 29/00 |
| 2018/0055838 A1 | 3/2018 | Zagon et al. |
| 2018/0228728 A1 | 8/2018 | Valia |
| 2019/0175519 A1 | 6/2019 | Haynes et al. |
| 2024/0165105 A1 | 5/2024 | Shudo et al. |

FOREIGN PATENT DOCUMENTS

| | | |
|---|---|---|
| CN | 101732313 A | 6/2010 |
| CN | 102946870 A | 2/2013 |
| CN | 105832687 A | 8/2016 |
| EP | 0709088 B1 | 5/1997 |
| EP | 0790058 A1 | 8/1997 |
| JP | S61-158924 A | 7/1986 |
| WO | WO2004075877 A1 | 9/2004 |
| WO | WO2015095644 A1 | 6/2015 |
| WO | WO2016149077 A2 | 9/2016 |
| WO | WO2017048595 A1 | 3/2017 |
| WO | WO2017053936 A1 | 3/2017 |
| WO | WO2017053938 A1 | 3/2017 |
| WO | WO2017125455 A1 | 7/2017 |

OTHER PUBLICATIONS

Biglardi et al., Treatment of pruritus with topically applied opiate receptor antagonist, J Am Acad Dermatol, Jun. 2007; 56(6):979-88.

Chiang et al., Pharmacokinetics of the combination tablet of buprenorphine and naloxone, Drug Alcohol Depend. May 21, 2003; 70(2 Suppl):S39-47.

Cruciani et al., Ultra-Low Dose Oral Naltrexone Decreases Side Effects and Potentiates the Effect of Methadone, Jun. 2003, vol. 25, Issue 6, pp. 491-494.

Culpepper-Morgan et al., Treatment of opioid-induced constipation with oral naloxone: a pilot study, Clin Pharmacol Ther, Jul. 1992; 52(1):90-5.

Goldberg et al., Acute and chronic effects of naltrexone and naloxone on schedule-controlled behavior of squirrel monkeys and pigeons, J Pharmacol Exp Ther, Mar. 1981; 216(3):500-9.

Harris et al., Buprenorphine and naloxone co-administration in opiate-dependent patients stabilized on sublingual buprenorphine, Drug Alcohol Depend, Dec. 22, 2000; 61(1):85-94.

Holzer, New approaches to the treatment of opioid-induced constipation, Eur Rev Med Pharmacol Sci. Aug. 2008;12 Suppl 1:119-27.

Hughes et al., Principles of early drug discovery, Br J Pharmacol. Mar. 2011; 162(6):1239-1249.

Hussain et al., Buccal and oral bioavailability of naloxone and naltrexone in rats, International Journal of Pharmaceutics vol. 36, Issues 2-3, May 1987, pp. 127-130.

Kreek et al., Naloxone, a specific opioid antagonist, reverses chronic idiopathic constipation, Lancet. Feb. 5, 1983; 1(8319):261-2.

Largent-Milnes et al., Oxycodone Plus Ultra-Low-Dose Naltrexone Attenuates Neuropathic Pain and Associated μ-Opioid Receptor-Gs Coupling, Aug. 2008, vol. 9, Issue 8, pp. 700-713.

Liu et al., Low-Dose Oral Naloxone Reverses Opioid-Induced Constipation and Analgesia, J Pain Symptom Manage. Jan. 2002; 23(1):48-53.

Nasser et al., Pharmacokinetics of Sublingual Buprenorphine and Naloxone in Subjects with Mild to Severe Hepatic Impairment (Child-Pugh Classes A, B, and C), in Hepatitis C Virus-Seropositive Subjects, and in Healthy Volunteers, Clin Pharmacokinet. Aug. 2015; 54(8):837-49.

Nelson et al., Opioid-induced constipation: advances and clinical guidance, Ther Adv Chronic Dis. Mar. 2016; 7(2):121-134.

Ngai et al., Pharmacokinetics of naloxone in rats and in man: basis for its potency and short duration of action. Anesthesiology, May 1976; 44(5):398-401.

Panchagnula et al., Transdermal delivery of naloxone: skin permeation, pharmacokinetic, irritancy and stability studies, Int J Pharm. Apr. 11, 2005; 293(1-2):213-23.

Pereira et al., Does naloxone reinstate secondary hyperalgesia in humans after resolution of a burn injury? A placebo-controlled, double-blind, randomized, cross-over study, PLOS One www.plosone.org May 1, 2013 vol. 8 Issue 5 e64608.

Pereira et al., Effect of a high-dose target-controlled naloxone infusion on pain and hyperalgesia in patients following groin hernia repair: study protocol for a randomized controlled trial, Trials. Nov. 10, 2015; 16:511.

Pereira et al., How to define chronic prurigo?, Experimental Dermatology, Dec. 2019, 28(12): 1455-1460.

Piercey et al., Naloxone inhibits the anti-diarrhoeal activity of loperamide, Br J Pharmacol. Jul. 1979; 66(3):373-375.

Poelaert et al., Treatment with prolonged-release oxycodone/naloxone improves pain relief and opioid-induced constipation compared with prolonged-release oxycodone in patients with chronic severe pain and laxative-refractory constipation, Clin Ther. Apr. 1, 2015; 37(4):784-92.

Poulsen et al., Clinical potential of naloxegol in the management of opioid-induced bowel dysfunction, Clin Exp Gastroenterol. Sep. 19, 2014; 7:345-58.

Smith et al., Single- and multiple-dose pharmacokinetic evaluation of oxycodone and naloxone in an opioid agonist/antagonist prolonged-release combination in healthy adult volunteers, Clin Ther. Nov. 2008; 30(11):2051-68.

Swegle et al., Management of common opioid-induced adverse effects, Am Fam Physician, Oct. 15, 2006, 74(8):1347-54.

Tsai et al., Molecular weight dependence of polyethylene glycol penetration across acetone-disrupted permeability barrier, Arch Dermatol Res, Jun. 2001; 293(6):302-7; Abstract only.

Tsai et al., Ultra-low-dose naloxone enhances the antinociceptive effect of morphine in PTX-treated rats: regulation on global histone methylation, Acta Anaesthesiol Taiwan. Sep. 2012; 50(3):106-11.

Wang et al., Ultra-low-dose naloxone suppresses opioid tolerance, dependence and associated changes in mu opioid receptor-G protein coupling and Gbetagamma signaling, Neuroscience. 2005; 135(1):247-61.

Wong et al., Inflammatory and Noninflammatory Itch: Implications in Pathophysiology-Directed Treatments, Int J Mol Sci. Jul. 2017; 18(7):1485.

Definition of "several" accessed online at www.mirriam-webster.com on Nov. 25, 2019 (Year: 2019).

Definition of "homogeneous" accessed online at www.mirriam-webster.com on Jun. 2, 2021 (Year: 2021).

Topical Dosage Form Excipients, Croda Inc, Apr. 21, 2010, PN-40R-10, 7 pages.

Super Refined PEGs, Croda Inc, Apr. 2017, 3 pages.

Super Refined PEG 400, Croda Inc, Jun. 8, 2017, PN-073R-4, 7 pages.

Super Refined PEG 400, Croda Inc, Jul. 22, 2015, PN-073R-3, 7 pages.

Stability of APIs in Super Refined PEG, Croda Inc, Mar. 2018, 4 pages.

(56) References Cited

OTHER PUBLICATIONS

Purity of PEG 400 Effects the Stability of Gelatin Capsules, Poster Presentation, 2005 American Association of Pharmaceutical Scientists, Annual Meeting and Exposition, Nov. 6-10, Nashville, TN, 2 pages.

Purity of PEG 400 Affects API Stability, Croda Inc, Poster Presentation, 2006 American Association of Pharmaceutical Scientists, Annual Meeting and Exposition, Oct. 29-Nov. 2, San Antonio, TX, 3 pages.

The Power of Excipient Purity in API Stability, Croda Inc, Mar. 2018, 6 pages.

Carbowax Sentry Polyethylene Glycols, Dow Pharma Solutions, Sep. 2016, 8 pages.

Xu et al., Synergistic effects of ethosomes and chemical enhancers on enhancement of naloxone permeation through human skin, Pharmazie, 2007, 62:316-318.

\* cited by examiner

Comparison of naloxone ointment made with PEG300/PEG1450 at 25 °C

Comparison of naloxone ointment made with PEG400/PEG1450 at 25 °C

FIG. 3
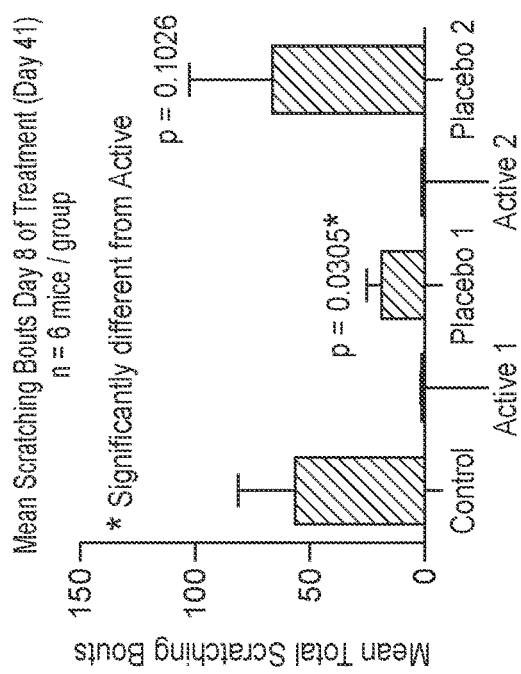
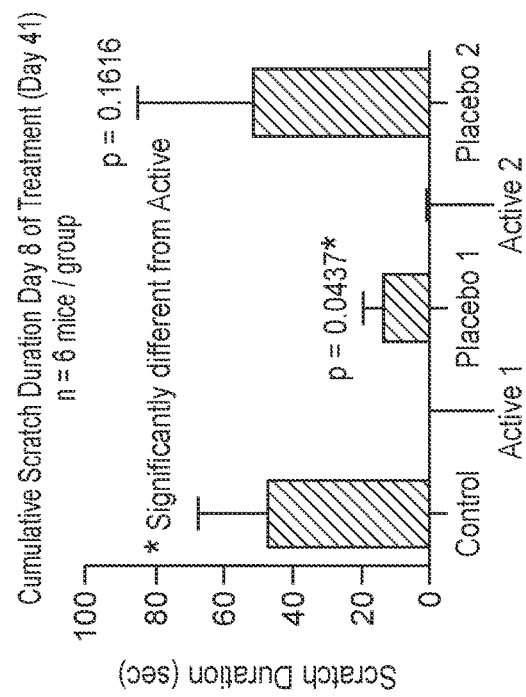
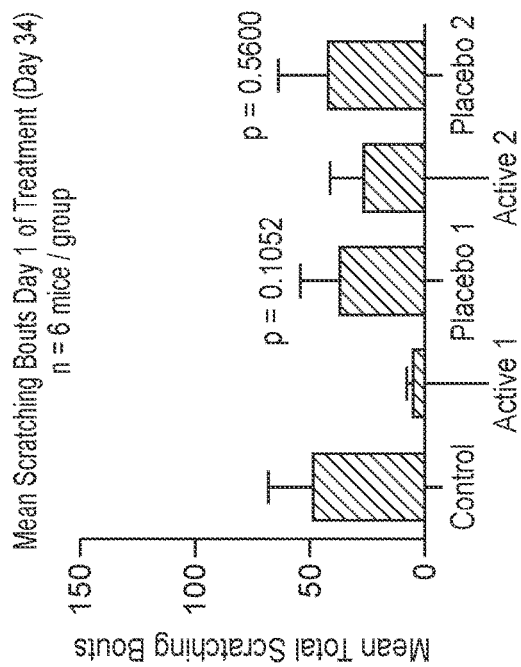
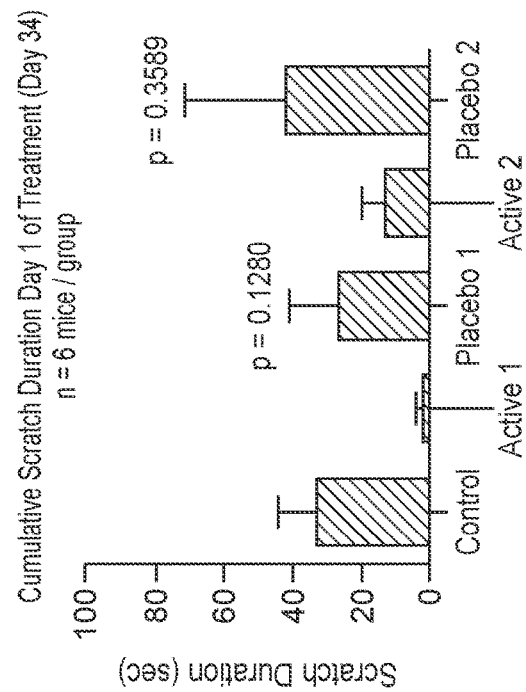

FIG. 9A Active 2: Naloxone base/PEG300/Shea XP
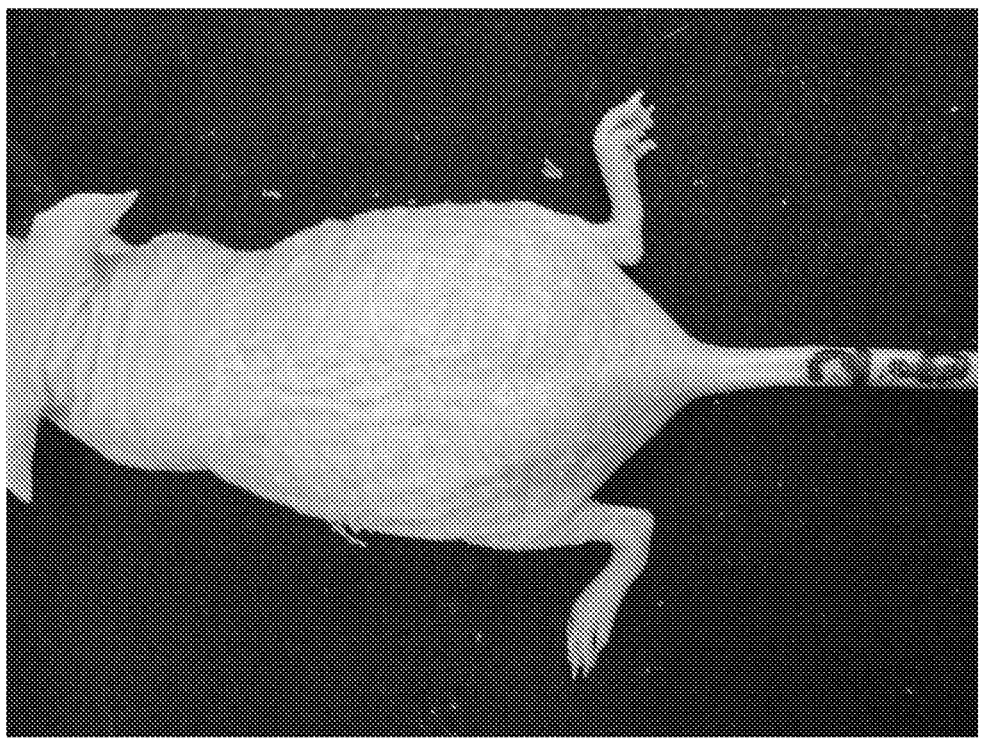
FIG. 9B Placebo 2: PEG300/Shea XP Placebo 5: PEG 300/PEG1450

Active 5: Naloxone HCl/PEG 300/PEG1450

TOPICAL NALOXONE COMPOSITIONS AND METHODS FOR USING THE SAME

CROSS REFERENCE TO RELATED APPLICATION

This application is a U.S. National Stage Application of PCT Application No. PCT/US2021/017550 filed Feb. 11, 2021, which application, pursuant to 35 U.S.C. § 119(e), claims priority to the filing date of U.S. Provisional Patent Application Ser. No. 62/976,967, filed Feb. 14, 2020; the disclosures of which applications are herein incorporated by reference.

INTRODUCTION

Naloxone is a narcotic μ-opioid receptor (MOR) antagonist having a high affinity for the μ-opioid receptors in the central nervous system. The μ-opioid receptors are a class of opioid receptors with affinity for enkephalins and beta-endorphin but low affinity for dynorphins. The three well characterized variants of the μ-opioid receptors are $\mu_1$, $\mu_2$ and $\mu_3$ which are typically found pre-synaptically (e.g., in the periaqueductal gray region and in the superficial dorsal horn of the spinal cord) or post-synaptically. Activation of μ-opioid receptors (such as with an agonist) can lead to analgesia, sedation, reduced blood pressure, itching, nausea, euphoria, decreased respiration and miosis. The κ-opioid receptors can also be found in the intestinal tract and activation of these receptors can sometimes inhibit peristaltic action resulting in constipation. Naloxone, also known commercially as Narcan® or Evzio®, also has lower affinity at the κ-opioid receptor and the δ-opioid receptor.

Naloxone is typically administered parenterally, such as by intravenous injection or infusion, which administration route provides for rapid delivery of the drug and complete bioavailability, thus making this route predictable and controllable. Solution formulations for parenteral administration must be essentially free of particulate matter, and they must be sterile. They must be physically and chemically stable, so that efficacy and safety are predictable.

SUMMARY

Aspects of the invention include topical naloxone compositions for locally delivering naloxone to the skin of a subject. Topical compositions according to certain embodiments are storage stable non-aqueous topical compositions that include naloxone free base and a non-aqueous vehicle, wherein the compositions are substantially free of naloxone N-oxide. Also provided are methods of using the topical compositions to locally deliver naloxone to a subject, as well as kits containing the topical naloxone compositions.

BRIEF DESCRIPTION OF THE FIGURES

FIG. 3 depicts the mean scratching bouts and cumulative scratching duration exhibited by mice at days 34 and 41 applied with: 1) placebo (no naloxone active agent); 5 or 2) a topical composition having naloxone free base

FIGS. 9A-9B depict example photographs of the skin of mice applied with placebo (no naloxone active agent) compositions and topical compositions having naloxone free base and hydrophobic delivery vehicle.

DETAILED DESCRIPTION

Figure 1:
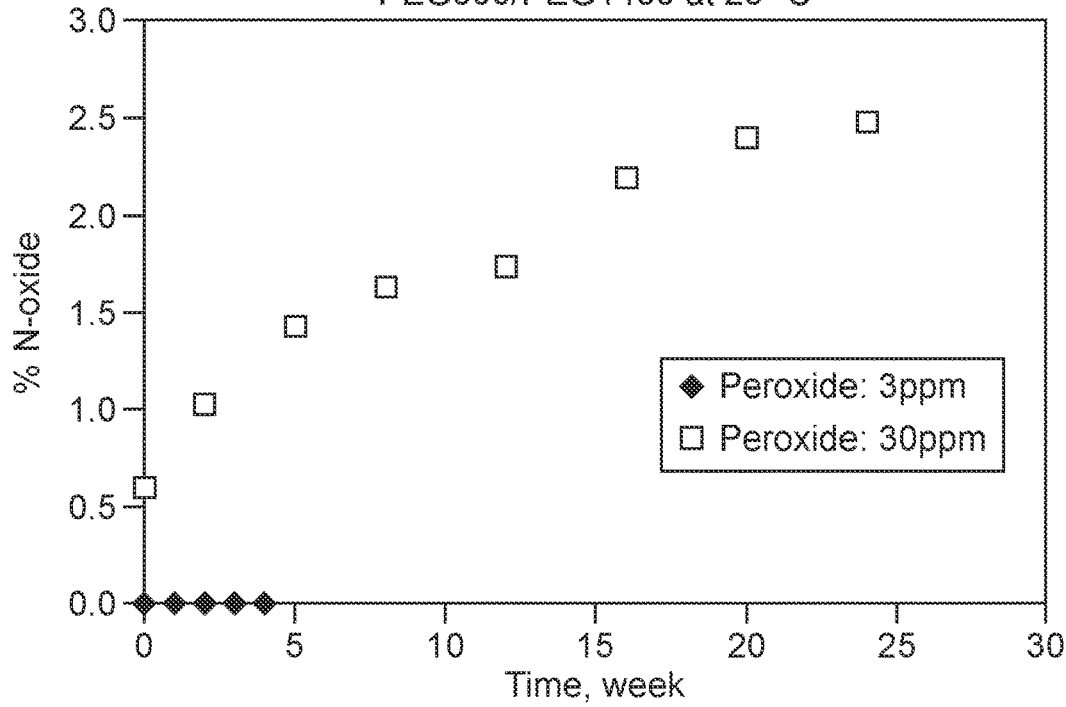
FIGS. 1 and 2 show observed percentages of naloxone N-oxide for each of various ointment formulations prepared from different PEG sources.

Aspects of the invention include topical naloxone compositions for locally delivering naloxone to the skin of a subject. Topical compositions according to certain embodiments are storage stable non-aqueous topical compositions that include naloxone free base and a non-aqueous vehicle, wherein the compositions are substantially free of naloxone N-oxide. Also provided are methods of using the topical compositions to locally deliver naloxone to a subject, as well as kits containing the topical naloxone compositions.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

In further describing various embodiments of the invention, aspects of the topical compositions are reviewed first in greater detail, followed by a detailed description of embodiments of using the topical compositions to deliver naloxone to a subject to treat a skin condition and a review of kits that include the subject topical naloxone compositions.

Topical Compositions

As summarized above, aspects of the invention include topical compositions for delivering an amount of naloxone free base to a subject. As such, the topical compositions include naloxone free base. The naloxone free base is described by the formula:

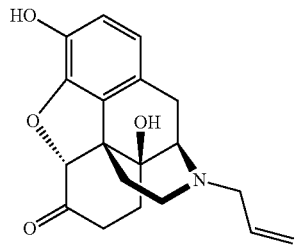

In embodiments, the subject naloxone compositions are formulated to topically deliver the naloxone free base to a subject. The term "topically" is used herein in its conventional sense to refer to the route of administration where the naloxone free base is delivered across the surface of the skin, such as delivered to one or more of the subcutis, dermis and epidermis, including the stratum corneum, stratum germinativum, stratum spinosum and stratum basale. Accordingly, topical compositions having a naloxone free base are formulated to be applied at any convenient location, such as for example, the arms, legs, buttocks, abdomen, back, neck, scrotum, face, behind the ear, etc. In some embodiments, the skin is healthy intact skin. In other embodiments, the skin may be skin where one or more layers (e.g., stratum corneum, stratum germinativum, stratum spinosum, stratum basale, etc.) may be diseased, inflamed or not fully intact. The phrase "not fully intact" is used herein in its conventional sense to mean that the one or more layers of not fully intact skin includes at least one perforation resulting from disease, inflammation or other condition, where not fully intact skin may include defective barrier properties in one or more layers of the skin (e.g., perforations) such as in the stratum corneum that is cumulatively 0.01% or more of the surface area where the topical naloxone composition is applied, such as 0.05% or more, such as 0.1% or more, such as 0.5% or more, such as 1% or more, such as 2% or more, such as 3% or more, such as 5% or more, such as 10% or more, such as 25% or more, such as 50% or more, such as 75% or more, such as 90% or more, such as 95% or more, such as 97% or more and including 99% or more of the surface area where the topical naloxone composition is applied.

In certain embodiments, the naloxone free base is delivered locally to the site of administration. The term "locally" is used herein in its conventional sense to mean that naloxone is delivered within the vicinity or underlying vicinity of the application site. In these embodiments, the naloxone free base diffuses from the application site by a predetermined distance, such as 30 cm or less, such as 25 cm or less, such as 20 cm or less, such as 15 cm or less, such as 10 cm or less, such as 5 cm or less, such as 4 cm or less, such as 3 cm or less, such as 2 cm or less, such as 1 cm or less, such as 0.5 cm or less and including within 0.1 cm or less from the application. In other words, in these embodiments the subject compositions are topically administered with the intention of delivering naloxone to a location at or within a small distance from the site of administration. The penetration depth of the naloxone free base locally into the skin at the site of application may also vary depending on the components of the hydrophilic delivery vehicle (as described below) and may be from 0.01 mm to 15 mm, such as from 0.05 mm to 14.5 mm, such as from 0.1 mm to 14 mm, such as from 0.5 mm to 13.5 mm, such as from 1 mm to 13 mm, such as from 1.5 mm to 12.5 mm, such as from 2 mm to 12 mm, such as from 2.5 mm to 11.5 mm, such as from 3 mm to 11 mm, such as from 3.5 mm to 10.5 mm, such as from 4 mm to 10 mm and including a penetration depth into the skin at the site of application of from 5 mm to 10 mm. In some instances, administration as described above may also result in systemic administration of naloxone, such as systemic administration of a low dose of naloxone.

In certain embodiments, topical compositions of interest are formulated for extended delivery of naloxone to the subject. The term "extended delivery" is used herein to refer to a composition formulated to deliver the naloxone over an extended period of time, such as over the course of hours, including 1 hour or longer, such as 2 hours or longer, such as 3 hours or longer, such as 4 hours or longer, such as 5 hours or longer, such as 6 hours or longer, such as 7 hours or longer. For the above ranges an upper limit period of time is, in some instances, 10 hours or shorter, such as 9 hours or shorter, such as 8 hours or shorter, such as 7 hours or shorter. In certain embodiments, topical compositions are formulated to deliver naloxone to the subject for a period of time that ranges such as from 1 to 10 hours, such as from 2 hour to 9 hours, such as from 2 hours to 7 hours.

Depending on the site of application and physiology of the subject and surface area on the skin applied with the subject naloxone composition, the amount of the naloxone free base in topical compositions of interest may vary, in some instances, the amount of naloxone ranges from 0.01 mg to 2000 mg, such as from 0.02 mg to 1750 mg, such as from 0.03 mg to 1500 mg, such as from 0.04 mg to 1250 mg, such as 0.05 mg to 1000 mg, such as from 0.06 mg to 750 mg, such as from 0.07 mg to 500 mg, such as 0.08 mg to 250 mg, such as 0.09 mg to 100 mg, and including 0.01 mg to 50 mg. In some embodiments, the amount of the free base ranges from 1 mg to 200 mg, such as from 2.5 mg to 175 mg, such as from 5 mg to 150 mg, such as from 7.5 mg to 125 mg and including from 10 mg to 100 mg. In some embodiments, the amount of the naloxone free base is from 0.01% w/w to 15% w/w of the total weight of the topical composition, such as from 0.05% w/w to 12.5% w/w, such as from 0.05% w/w to 10% w/w, including 0.1% w/w to 10% w/w, such as from 0.1% w/w to 5% w/w, including 0.5% w/w to 5% w/w, such as from 0.75% w/w to 2.5% w/w. In some embodiments, the amount of naloxone free base in the topical composition is 0.5% w/w, 0.75% w/w, 1% w/w, 1.5% w/w, 2% w/w, 2.5% w/w, 3% w/w, 3.5% w/w, 4% w/w, 4.5% w/w, 5% w/w, 5.5% w/w, 6% w/w, 6.5% w/w, 7% w/w, 7.5% w/w, 8% w/w, 8.5% w/w, 9% w/w, 9.5% w/w or 10% w/w.

In addition, the compositions are substantially free of naloxone N-oxide. Naloxone N-oxide has the molecular formula: $C_{19}H_{21}NO_5$ and is described by the structural formula:

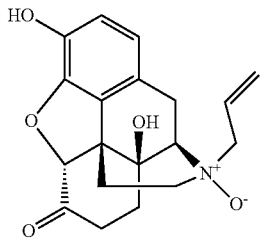 [SMILES: C=CC[N+]1([O-])CC[C@]23c4c5ccc(O)c4O[C@H]2C(=O)CC[C@@]3(O)[C@H]1C5]

As the compositions are substantially free of naloxone N-oxide, the amount of naloxone-N-oxide in the composition, if present, is 0.5% w/w or less, such as 0.2% w/w or less and including 0.1% w/w or less. In some instances, the compositions include no detectable naloxone-N-oxide, such that naloxone-N-oxide cannot be detected in the formulation using the protocol described in the Experimental section, below.

In some instances, the compositions are storage stable. Storage stable compositions of embodiments of the invention are substantially free of naloxone N-oxide even after storage under storage conditions, e.g., packaged sterile conditions at room temperature, for a period of time, e.g., 1 month longer, such as 3 months or longer, including 6 months or longer, e.g., 12 months or longer. In some instances, the topical formulations are storage stable, such that the composition and/or active agent properties, e.g., color, viscosity, active agent activity, etc., are not substantially altered over extended periods of time, e.g., 1 week or longer, 2 weeks or longer, 1 month or longer, 6 months or longer, 1 year or longer, under room and elevated temperatures, e.g., 40° C. or greater, including 50° C. or greater.

Topical compositions in accordance with embodiments of the invention include non-aqueous topical delivery vehicle. By "topical delivery vehicle" is meant a composition which carries and brings the naloxone free base into contact with and through the skin of the subject. In embodiments, the subject topical compositions are non-aqueous. As the topical delivery vehicle is non-aqueous, the vehicle does not include water, e.g., as a solvent. As such, the vehicle (a composition that includes the vehicle and naloxone free base) includes no water.

In some instances, the non-aqueous vehicle includes a polyethylene glycol component. The term "polyethylene glycol" is used herein in its conventional sense to refer to polymeric compounds having an ethylene oxide backbone structure, such as linear polyethylene glycols, branched polyethylene glycols, functionalized linear polyethylene glycols or multi-functionalized branched polyethylene glycols or any combination thereof.

Topical delivery vehicle compositions of interest include a polyethylene glycol component having a polyethylene glycol having an average molecular weight (e.g., a U.S. Pharmacopeia-specified molecular weight) of from 100 g/mol to 7500 g/mol, such as from 150 g/mol to 5000 g/mol, such as from 200 g/mol to 2500 g/mol, such as from 300 g/mol to 1500 g/mol. The term "average molecular weight" is used in its conventional sense to refer to the total weight of polymer divided by the total number of molecules. In some embodiments, the polyethylene glycol component includes a polyethylene glycol having an average molecular weight of from 200 g/mol to 2000 g/mol, such as 300 g/mol or 400 g/mol to 1500 g/mol. The average molecular weight of the polyethylene glycol may be determined by any suitable molecular weight determination protocol, including but not limited to titration, size exclusion chromatography, high performance liquid chromatography, gel permeation chromatography, mass spectrometry, among other protocols.

The polyethylene glycol component may include one or more different types of polyethylene glycols, such as 2 or more different types of polyethylene glycols, such as 3 or more different types of polyethylene glycols, such as 4 or more different types of polyethylene glycols, such as 5 or more different types of polyethylene glycols and including 10 or more different types of polyethylene glycols. In certain embodiments, the polyethylene glycol component in the subject naloxone compositions includes a first polyethylene glycol and a second polyethylene glycol. In some such embodiments, the polyethylene glycol component may include a first polyethylene glycol that is a liquid below room temperature (RT) (e.g., PEG600 and below) and a second polyethylene glycol that is a waxy solid at RT or above RT (e.g., PEG 1000 and above). In some embodiments, the first polyethylene glycol component is a lower molecular weight polyethylene glycol having an average molecular weight of 1000 g/mol or less and the second polyethylene glycol component is a higher molecular weight polyethylene glycol having an average molecular weight of 1000 g/mol or greater. For example, the first polyethylene glycol component may be a polyethylene glycol having an average molecular weight of 600 g/mol or less, such as 550 g/mol or less, such as 500 g/mol or less, such as 450 g/mol or less, such as 400 g/mol or less, such as 350 g/mol or less, such as 300 g/mol or less. For instance, the first polyethylene glycol component is a polyethylene glycol that has an average molecular weight that ranges from 200 g/mol to 600 g/mol, such as from 250 g/mol to 500 g/mol, such as from 300 g/mol to 400 g/mol. In certain embodiments, the first polyethylene glycol component is a polyethylene glycol having an average molecular weight of 300 g/mol. In certain embodiments, the first polyethylene glycol component is a polyethylene glycol having an average molecular weight of 400 g/mol. The second polyethylene glycol component may be a polyethylene glycol having an average molecular weight of 1000 g/mol or greater, such as 1050 g/mol or greater, such as 1100 g/mol or greater, such as 1150 g/mol or greater, such as 1200 g/mol or greater, such as 1250 g/mol or greater, such as 1300 g/mol or greater, such as 1350 g/mol or greater, such as 1400 g/mol or greater, such as 1450 g/mol or greater and including a polyethylene glycol having an average molecular weight of 1500 g/mol or greater. For instance, the second polyethylene glycol component may be a polyethylene glycol having an average molecular weight that ranges from 1000 to 6000 g/mol, such as from 1100 g/mol to 4000 g/mol, such as from 1200 g/mol to 3000 g/mol, such as from 1300 g/mol to 2000 g/mol and including from 1400 g/mol to 1500 g/mol. In certain embodiments, the second polyethylene glycol component is a polyethylene glycol having an average molecular weight of 1450 g/mol. With respect to the total amount of polyethylene glycols that are present, the percentage that is the first molecular weight polyethylene glycol, e.g., 300 or 500 g/mol, may vary, ranging in some instances from 20 to 90%, such as 30 to 70% including 50 to 70%. The percentage that is the second molecular weight polyethylene glycol, e.g., 1450 g/mol, may vary, ranging in some instances from 20 to 50%, such as 30 to 45%. Where a first lower molecular weight polyethylene glycol is combined with a second higher molecular weight polyethylene glycol, the compositions may include more of the first polyethylene glycol than the second polyethylene glycol, e.g., where the amount of the first lower molecular weight polyethylene glycol may exceed the amount of second higher molecular weight polyethylene glycol, e.g., by 2% or more, such as 5% or more, including 10% or more.

In some instances, the storage stable non-aqueous topical compositions include 0.1 to 1% by weight naloxone free base, 50 to 70% by weight of a first polyethylene glycol having an average molecular weight of 300 to 400 g/mol and 30 to 45% by weight of a second polyethylene glycol having an average molecular weight of 1450 g/ml. Formulations of interest include:

0.1% naloxone free base/60-65% PEG400/39.9-34.9% PEG1450
0.5% naloxone free base/60-65% PEG400/39.5-34.5% PEG1450
1% naloxone free base/60-65% PEG400/39-34% PEG1450.

In some embodiments, the polyethylene glycol(s) is a pharmaceutical grade polyethylene glycol having a molecular weight certified (i.e., with a Certificate of Analysis) by a regulatory agency (e.g., U.S. Pharmacopeia, USP and National Formulary, the European Pharmacopoeia, etc.) In some instances, at least the first polyethylene glycol component is one that includes little or no peroxides at the time the composition is prepared, e.g., 50 ppm or less, such as 40 ppm or less, including 30 ppm or less, including 20 ppm or less, including 10 ppm or less, including 5 ppm or less, including 1 ppm or less. Commercially available polyethylene glycols that may be employed in embodiments of the invention include: Super Refined™ polyethylene glycols (Croda, East Yorkshire, England), Emprove® Millipore polyethylene glycols (Merck KGaA, Darmstadt, Germany); Pluriol® polyethylene glycols (BASF); Japanese Pharmacopoeia Macrogol polyethylene glycols (NOF Corporation); and the like.

Where desired, the non-aqueous delivery vehicle may include one or more anti-oxidants. When present, the one or more anti-oxidants may vary in amount, ranging in amount in some instances from 0.01 to 5.0% w/w, such as from 0.02 to 2.0% w/w. Any convenient anti-oxidant that reduces the occurrence of impurities, e.g., as described in the experimental section below, may be present, where examples of such anti-oxidants include: butylated hydroxytoluene (BHT); propyl gallate; etc.

The amount of non-aqueous delivery vehicle (e.g., PEG) present in the topical naloxone composition may vary and may range from 90% w/w to 99.9% w/w, such as from 95% w/w to 99.9% w/w, such as from 99% w/w to 99.9% w/w.

The topical naloxone compositions may vary as desired. In some instances, the topical naloxone composition is an ointment. The term "ointment" is used to refer to a semisolid preparation intended for external application to the skin or mucous membranes. In some instances, ointments exhibit a loss on drying of 25% or less, such as 20% or less. In some instances, ointments exhibit a viscosity ranging from 300,000 to 2,000,000 cp, such as 350,000 to 1,800,000 cp, including 400,000 to 1,700,000 cp. In some instances, the topical naloxone composition is a cream. The term "cream" is used to refer to semisolid dosage form containing one or more drug substances dissolved or dispersed in a suitable base. In some instances, creams exhibit a viscosity ranging from 25,000 to 900,000 cp, such as 30,000 to 800,000 cp, including 50,000 to 700,000 cp. In some instances, the topical naloxone composition is a lotion. The term "lotion" refers topical suspensions, solutions and emulsions intended for application to the skin. In some instances, lotions exhibit a loss on drying of 40% or more, such as 50% or more. In some instances, lotions are pourable, and exhibit a viscosity ranging from 1,000 to 50,000 cp, such as 2,000 to 40,000 cp, including 5,000 to 30,000 cp. In some instances, the topical naloxone composition is a gel. The term "gel" refers to a semisolid system consisting of either suspensions made up of small inorganic particles or large organic molecules interpenetrated by a liquid. In some instances, gels exhibit a loss on drying of 60% or more, such as 70% or more. In some instances, gels exhibit a viscosity ranging from 5,000 to 100,000 cp, such as 5,000 to 70,000 cp. In certain instances, the topical naloxone composition is formulated as a liquid and may be dispensed as a spray, aerosol or foam.

Topical naloxone compositions according to embodiments of the invention are non-irritating to the skin of the subject at the site of application. Irritation of the skin is referred to herein in its general sense to refer to adverse effects, discoloration or damage to the skin, such as for example, redness (erythema), pain, swelling (edema) or dryness. As such, the subject topical compositions are formulated such that when applied to the skin of a subject, the quality of the skin remains normal and local delivery of naloxone remains consistent throughout the entire dosage interval.

In some embodiments, topical naloxone compositions are formulated to locally deliver a predetermined amount of the naloxone through one or more layers of the skin of the subject.

In certain embodiments, the subject topical naloxone compositions may be first applied to a patch and applied to the skin site on the subject or a patch may be positioned on top of the skin site that is applied with the topical naloxone composition. The patch may be fabricated from a material that does not absorb the naloxone. Patches of interest include, but are not limited to, non-woven fabrics, woven fabrics, films (including sheets), porous bodies, foamed bodies, paper, composite materials obtained by laminating a film on a non-woven fabric or fabric, and combinations thereof. Non-woven fabrics may include polyolefin resins such as polyethylene and polypropylene; polyester resins such as polyethylene terephthalate, polybutylene terephthalate and polyethylene naphthalate; rayon, polyamide, poly (ester ether), polyurethane, polyacrylic resins, polyvinyl alcohol, styrene-isoprene-styrene copolymers, and styrene-ethylene-propylene-styrene copolymers; and combinations thereof. Fabrics may include cotton, rayon, polyacrylic resins, polyester resins, polyvinyl alcohol, and combinations thereof. Films may include polyolefin resins such as polyethylene and polypropylene; polyacrylic resins such as polymethyl methacrylate and polyethyl methacrylate; polyester resins such as polyethylene terephthalate, polybutylene terephthalate and polyethylene naphthalate; and besides cellophane, polyvinyl alcohol, ethylene-vinyl alcohol copolymers, polyvinyl chloride, polystyrene, polyurethane, polyacrylonitrile, fluororesins, styrene-isoprene-styrene copolymers, styrene-butadiene rubber, polybutadiene, ethylene-vinyl acetate copolymers, polyamide, and polysulfone; and combinations thereof. Papers may include impregnated paper, coated paper, wood free paper, Kraft paper, Japanese paper, glassine paper, synthetic paper, and combinations thereof. In some embodiments, the patch is an occlusive material.

The size of the patch may vary depending on the area on the skin applied with the topical naloxone composition, and in some instances the patch is sized to cover the entire application site on the subject. As such, the patch may have a length ranging from 2 to 100 cm, such as 4 to 60 cm and a width ranging from 2 to 100 cm, such as 4 to 60 cm. The surface area of patches of interest may range from 4 cm$^2$ to 1000 cm$^2$, such as from 5 cm$^2$ to 500 cm$^2$, such as from 10 cm$^2$ to 250 cm$^2$, such as from 15 cm$^2$ to 100 cm$^2$ and including from 20 cm$^2$ to 50 cm$^2$.

Methods for Applying Topical Naloxone Compositions

Aspects of the invention also include methods for applying topical naloxone compositions of the invention to a subject. As discussed above, topical refers to the route of administration where naloxone is delivered across the skin, such as delivered to one or more of the subcutis, dermis and epidermis, including the stratum corneum, stratum germinativum, stratum spinosum and stratum basale. Accordingly, methods may include applying the subject naloxone compositions to a skin site on the arms, legs, buttocks, shoulders, hips, thighs, abdomen, back, neck, scrotum, face, behind the ear, etc. In some embodiments, methods include applying the subject compositions to healthy intact skin. In other embodiments, methods include applying the subject compositions to skin where one or more layers (e.g., stratum corneum, stratum germinativum, stratum spinosum, stratum basale, etc.) may be diseased, inflamed or not fully intact, such as skin that includes defective barrier properties in one or more layers (e.g., perforations), such as in the stratum corneum resulting from disease, inflammation or other condition. For example, methods may include applying to a skin surface of a subject where the skin includes defective barrier properties (e.g., perforations) in one or more layers that is cumulatively 0.01% or more of the surface area where the topical naloxone composition is applied, such as 0.05% or more, such as 0.1% or more, such as 0.5% or more, such as 1% or more, such as 2% or more, such as 3% or more, such as 5% or more, such as 10% or more, such as 25% or more, such as 50% or more, such as 75% or more, such as 90% or more, such as 95% or more, such as 97% or more and including 99% or more of the surface area where the topical naloxone composition is applied.

In describing methods of the present invention, the term "subject" is meant the person or organism to which the topical composition is applied and maintained in contact. As such, subjects of the invention may include but are not limited to mammals, e.g., humans and other primates, such as chimpanzees and other apes and monkey species, dogs, rabbits, cats and other domesticated pets; and the like, where in certain embodiments the subject are humans. The term subject is also meant to include a person or organism of any age, weight or other physical characteristic, where the subjects may be an adult, a child, an infant or a newborn.

As described above, methods of the invention include applying a topical naloxone composition to a skin surface of a subject and maintaining the topical composition in contact with the subject over a period of time sufficient to deliver naloxone to the subject. In some embodiments, methods include extended delivery of naloxone to the skin site of the subject. By "extended transdermal delivery" is meant that the topical composition is formulated to provide for delivery of naloxone over an extended period of time, such as over the course of hours, including 1 hour or longer, such as 2 hours or longer, such as 3 hours or longer, such as 4 hours or longer, such as 5 hours or longer and including 6 hours or longer, e.g., 7 hours or longer. For example, the topical composition may be formulated to deliver naloxone to the skin site of the subject for a duration of from 0.1 hours to 20 hours, such as from 0.5 hours to 15 hours, such as from 1 hour to 10 hours, such as from 2 hours to 7 hours.

In certain embodiments, protocols may include multiple dosage intervals. By "multiple dosage intervals" is meant that two or more dosages of the topical composition are applied and maintained in contact with the subject in a sequential manner. As such, the first application of the topical composition is removed from contact with the subject (e.g., washed away with water or wiped clean with a damp cloth) and a second dosage of the topical composition is applied to the skin surface of the subject. In practicing methods of the invention, treatment regimens may include two or more dosage intervals, such as three or more dosage intervals, such as four or more dosage intervals, such as five or more dosage intervals, including ten or more dosage intervals.

The duration between dosage intervals in a multiple dosage interval treatment protocol may vary, depending on the physiology of the subject or by the treatment protocol as determined by a health care professional. For example, the duration between dosage intervals in a multiple dosage treatment protocol may be predetermined and follow at regular intervals. As such, the time between dosage intervals may vary and may be 1 hour or longer, such as 2 hours or longer, such as 4 hours or longer, such as 6 hours or longer, such as 8 hours or longer, such as 12 hours or longer, such as 16 hours or longer and including 24 hours or longer. In certain embodiments, multiple dosage interval protocols provide for a time between dosage intervals of 1 day or longer, such as 2 days or longer, such as 3 days or longer, such as 4 days or longer, such as 5 days or longer, such as 6 days or longer, such as 7 days or longer, such as 10 days or longer, including 30 days or longer. An upper limit period of time between dosage intervals is, in some instances, 30 days or shorter, such as 28 days or shorter, such as 21 days or shorter, such as 14 days or shorter, such as 7 days or shorter and including 3 days or shorter. In certain embodiments, the time between dosage intervals ranges such as from 2 days to 30 days, such as from 3 days to 28 days, such as from 4 days to 21 days, such as from 5 days to 14 days and including from 6 days to 10 days. In certain instances, the duration between dosage intervals may depend on the progress of treatment of a particular condition (as described in greater detail below), skin irritability, skin dryness or the extent to which symptoms of the treated condition are alleviated (e.g., reduction in itch).

Methods for applying and maintaining a topical naloxone composition in contact with a subject according to certain embodiments find use in the treatment or prevention of a skin condition, such as an inflammatory skin disease, a non-inflammatory skin disease, pruritis or one or more symptoms associated the inflammatory skin disease, non-inflammatory skin disease or pruritis. For example, methods in some instances include applying the topical composition to the skin surface of a subject to treat or prevent an inflammatory skin disease, such as atopic dermatitis, eczema, psoriasis, or a combination thereof. In other instances, methods include applying the topical composition to the skin surface of a subject to treat or prevent a non-inflammatory skin disease, such chronic prurigo. In yet other instances, methods include topically treating or preventing pruritus by applying to the skin of a subject one or more of the topical naloxone compositions described above. In certain instances, the pruritis is pruritus associated with one or more of primary biliary cirrhosis, chronic renal failure, renal dialysis, abnormal blood pressure, thyroid gland malfunction, aging, cancer, anemia, a parasite, a neurological condition or pregnancy. In certain embodiments, the pruritus is a drug-induced pruritus or a pruritogen-induced pruritus. In certain embodiments, the pruritis is associated with a condition selected from shingles, psoriasis, hives, notalgia paresthetica, Grover's disease, chronic kidney disease and Hailey-Hailey disease. The pruritus may be accompanied by skin redness, skin bumps, spots or blisters, dry or cracked skin, leathery skin or scaly textured skin and methods may also include applying an amount of the subject naloxone composition sufficient to treat one or more of the skin redness, skin bumps, spots or blisters, dry or cracked skin, leathery skin or scaly textured skin that accompanies the pruritus.

In methods of treating a skin condition according to certain embodiments, the topical naloxone composition may be applied directly onto the affected area of the skin (e.g., the location of the inflammatory skin condition, non-inflammatory skin condition or pruritis). The topical composition may be applied to all or part of the affected area of the skin, such as 5% or more of affected area of the skin, such as 10% or more, such as 25% or more, such as 50% or more, such as 75% or more, such as 90% or more, such as 95% or more and including 99% or more. In some instances, the entire affected area of the skin is applied with the topical composition. In certain instances, an area greater that the affected area of the skin is applied with the topical composition, such as an amount of the skin surface immediately adjacent to the affected skin area, such as an additional 5% (based on the size of the diseased skin) or more of the surrounding area on the skin, such as an additional 10% or more, such as an additional 15% or more and including an additional 25% or more of surrounding area on the skin.

The term "treatment" is used herein in its conventional sense to mean that at least an amelioration of the symptoms associated with the condition afflicting the subject is achieved, where amelioration is used in a broad sense to refer to at least a reduction in the magnitude of a parameter, e.g., symptom, associated with the condition being treated. As such, treatment also includes situations where the pathological condition, or at least symptoms associated therewith, are completely eliminated, such that the subject no longer suffers from the condition, or at least the symptoms that characterize the condition. The term "manage" is used herein in its conventional sense to mean that the symptoms associated with the condition afflicting the subject are at least kept under control (i.e., magnitude of the symptom are kept within a predetermined level), where in some instances the symptoms are ameliorated without eliminating the underlying condition.

The term "prevention" is used herein in its conventional sense to mean the reduction or complete elimination of the occurrence of a particular condition, such as where the subject topical compositions are prophylactically applied to the skin surface of a subject and the indicated skin condition is altogether prevented from occurring or a reduction in the severity of the condition or symptoms associated with the conditions is experienced by the subject. Accordingly, methods according to certain embodiments include prophylactically applying the subject topical naloxone compositions sufficient to reduce the severity of the condition or symptoms associated with the condition by 5% or more as determined by a qualified health care professional (e.g., based on size of diseased skin, amount of inflammation, etc.), such as by 10% or more, such as by 15% or more, such as by 25% or more, such as by 50% or more, such as by 75% or more, such as by 90% or more, such as by 95% or more and including by 99% or more. In some embodiments, applying a topical naloxone composition according the subject methods is sufficient to altogether eliminate the occurrence of the condition or any symptoms associated with the skin disease. In some embodiments, prophylactically applying the topical naloxone composition to the skin surface of the subject is sufficient to reduce the duration of skin condition, such as by 0.1 days or more, such as by 0.5 days or more, such as by 1 day or more, such as by 2 days or more, such as by 3 days or more, such as by 4 days or more, such as by 5 days or more, such as by 6 days or more, such as by 7 days or more and including by 14 days or more. In other embodiments, prophylactically applying the topical naloxone composition to the skin surface of the subject is sufficient to reduce the severity of symptoms associated with the skin condition, such as an itch. For example, prophylactically applying the topical naloxone composition to the skin surface of the subject may be sufficient to reduce the number of times the skin surface is scratched in response to the skin condition by 1 time per hour or more, such as 2 times per hour or more, such as 3 times per hour or more, such as 5 times per hour or more, such as 10 times per hour or more, such as 15 times per hour or more, such as 25 times per hour or more, such as 50 times per hour or more and including 100 times per hour or more. Where methods include prophylactically treating pruritus, the topical naloxone composition may be applied onto a skin surface of the subject 1 hour or more before the onset of symptoms (e.g., itch, skin redness, scaliness, blisters or bumps, etc.) associated with the pruritus, such as 3 hours or more, such as 6 hours or more, such as 12 hours or more and including 24 hours or more because the onset of symptoms.

In embodiments, the topical composition may be prophylactically applied to the skin surface of the subject, 1 hour or more before a skin condition or associated symptoms thereof are anticipated (e.g., pruritus induced by a drug or pruritogen), such as 2 hours or more, such as 4 hours or more, such as 6 hours or more, such as 8 hours or more, such as 12 hours or more, such as 16 hours or more, such as 20 hours or more, such as 24 hours or more and including 48 hours or more.

In some embodiments, methods include applying to a skin surface of a subject a topical naloxone composition in the treatment or prevention of pruritus. The pruritus may be associated with one or more of primary biliary cirrhosis, chronic renal failure, renal dialysis, abnormal blood pressure, thyroid gland malfunction, aging, cancer, anemia, a parasite, a neurological condition, pregnancy or may be a drug-induced pruritus or a pruritogen-induced pruritus. In certain embodiments, the naloxone composition is formulated to treat or prevent one or more of skin redness, skin bumps, spots or blisters, dry or cracked skin, leathery skin or scaly textured skin that accompanies the pruritus. In these embodiments, applying the topical naloxone composition is sufficient to reduce the severity of the pruritus, such as by 5% or more (e.g., by patient-response survey, the number of times the skin surface is scratched in a predetermined time period), such as by 10% or more, such as by 15% or more, such as by 25% or more, such as by 50% or more, such as by 75% or more, such as by 90% or more, such as by 95% or more and including by 99% or more. In certain instances, applying and maintaining the topical naloxone composition in contact with the skin surface is sufficient to eliminate the pruritus. For example, applying the subject topical naloxone composition is sufficient to reduce the number of times the skin surface is scratched in response to the pruritus by 1 time per hour or more, such as 2 times per hour or more, such as 3 times per hour or more, such as 5 times per hour or more, such as 10 times per hour or more, such as 15 times per hour or more, such as 25 times per hour or more, such as 50 times per hour or more and including 100 times per hour or more. Where methods include prophylactically treating pruritus, the topical naloxone composition may be applied onto a skin surface of the subject 1 hour or more before the onset of symptoms (e.g., itch) associated with the pruritus, such as 3 hours or more, such as 6 hours or more, such as 12 hours or more and including 24 hours or more because the onset of symptoms.

In other embodiments, methods include applying skin surface of a subject a topical naloxone composition in the treatment or prevention of an inflammatory skin condition such as atopic dermatitis, eczema or psoriasis. In certain embodiments, the skin condition is atopic dermatitis that is associated with pruritus. In some instances, the naloxone composition is formulated to treat or prevent a symptom associated with the inflammatory skin condition, such as an itch caused by atopic dermatitis, eczema or psoriasis. In these embodiments, applying the topical naloxone composition is sufficient to reduce the severity of the symptom (e.g., itch) associated with the inflammatory skin condition, such as by 5% or more (e.g., by patient-response survey, the number of times the skin surface is scratched in a predetermined time period), such as by 10% or more, such as by 15% or more, such as by 25% or more, such as by 50% or more, such as by 75% or more, such as by 90% or more, such as by 95% or more and including by 99% or more. In certain instances, applying and maintaining the topical naloxone composition in contact with the skin surface is sufficient to eliminate the symptom (e.g., itch) associated with the inflammatory skin condition. For example, applying the subject topical naloxone composition is sufficient to reduce the number of times the skin surface is scratched in response to the itch caused by the inflammatory skin condition by 1 time per hour or more, such as 2 times per hour or more, such as 3 times per hour or more, such as 5 times per hour or more, such as 10 times per hour or more, such as 15 times per hour or more, such as 25 times per hour or more, such as 50 times per hour or more and including 100 times per hour or more.

In yet other embodiments, methods include applying to a skin surface of a subject a topical naloxone composition in the treatment or prevention of an inflammatory skin condition that is found to be partially or fully resistant to treatment by other active agents such as by steroidal treatment, an anti-inflammatory agent or an immunosuppressant. In these embodiments, applying the topical naloxone composition as described herein is sufficient to reduce the amount of steroid, anti-inflammatory agent or immunosuppressant administered to the subject to treat the skin condition, such as by 5% or more by weight, such as by 10% or more by weight, such as by 25% or more by weight, such as by 50% or more by weight, such as by 75% or more by weight, such as by 90% or more by weight and including by 95% or more by weight. In certain embodiments, applying and maintaining on the skin surface the subject topical naloxone composition is sufficient to entirely replace treatment of the inflammatory skin condition by a steroid, anti-inflammatory agent or an immunosuppressant.

In certain instances, methods include replacing one or more dosages of administered steroid treatment, anti-inflammatory agent or immunosuppressant in the treatment of an inflammatory skin condition (e.g., atopic dermatitis, eczema, psoriasis) by applying a topical naloxone composition as described herein, such as 2 or more, such as 3 or more, such as 4 or more, such as 5 or more, such as 6 or more, such as 7 or more, such as 8 or more, such as 9 or more, such as 10 or more, such as 15 or more, such as 25 or more, such as 50 or more, such as 75 or more and including 100 or more scheduled administrations of steroid treatment, anti-inflammatory agent or immunosuppressant to treat the inflammatory skin condition. As such, applying and maintaining the topical naloxone composition as described herein may be sufficient to reduce the number of scheduled administrations of steroid treatment, anti-inflammatory agent or immunosuppressant in treating an inflammatory skin condition by 5% or more, such as by 10% or more, such as by 15% or more, such as by 20% or more, such as by 25% or more, such as by 50% or more, such as by 75% or more, such as by 90% or more, such as by 95% or more and including reducing the number of scheduled administrations of steroid treatment, anti-inflammatory agent or immunosuppressant in treating an inflammatory skin condition by 99% or more.

In certain embodiments, the subject methods are suitable for entirely replacing steroid treatment, administration of an anti-inflammatory agent or immunosuppressant in treating an inflammatory skin condition with a topical naloxone composition as described herein.

In certain embodiments, methods include applying and maintaining one or more of the subject topical naloxone compositions in conjunction with steroid treatment, administration of an anti-inflammatory agent or immunosuppressant in treating an inflammatory skin condition. In some instances, a reduced dosage of steroid, anti-inflammatory agent or immunosuppressant may be administered to the subject in treating the inflammatory skin condition when the topical naloxone composition is in contact with the subject, such as where the dosage of each schedule administration of steroid, anti-inflammatory agent or immunosuppressant is reduced by 5% or more, such as by 10% or more, such as by 15% or more, such as by 20% or more, such as by 25% or more, such as by 50% or more and including by 75% or more. In some instances, one or more of the scheduled doses of steroid, anti-inflammatory agent or immunosuppressant administration is eliminated (i.e., skipped), such as every other scheduled dose, every 2 scheduled doses, every 3 scheduled doses, every 4 scheduled doses or some other interval. In certain instances, applying one of or more of the subject topical naloxone compositions is sufficient to eliminate sequential scheduled doses of steroid, anti-inflammatory agent or immunosuppressant, such as 2 or more sequentially scheduled doses, such as 3 or more sequentially scheduled doses and include 4 or more sequentially scheduled doses of steroid, anti-inflammatory agent or immunosuppressant.

In certain embodiments, compositions of the invention can be administered prior to, concurrent with, or subsequent to other therapeutic agents for treating the same or an unrelated condition. If provided at the same time as another therapeutic agent, the subject topical naloxone compositions may be administered in the same or in a different composition. Thus, naloxone compositions of interest and other therapeutic agents can be administered to the subject by way of concurrent therapy. By "concurrent therapy" is intended administration to a subject such that the therapeutic effect of the combination of the substances is caused in the subject undergoing therapy. For example, concurrent therapy may be achieved by administering naloxone compositions of the invention with a pharmaceutical composition having at least one other agent, such as an anti-inflammatory agent, immunosuppressant, steroid, analgesic, anesthetic, antihypertensive, chemotherapeutic, among other types of therapeutics, which in combination make up a therapeutically effective dose, according to a particular dosing regimen. Administration of the separate pharmaceutical compositions can be performed simultaneously or at different times (i.e., sequentially, in either order, on the same day, or on different days), so long as the therapeutic effect of the combination of these substances is caused in the subject undergoing therapy.

Where the naloxone composition is administered concurrently with a second therapeutic agent to treat the same condition, the weight ratio of naloxone to second therapeutic agent may range from 1:2 and 1:2.5; 1:2.5 and 1:3; 1:3 and 1:3.5 1:3.5 and 1:4; 1:4 and 1:4.5; 1:4.5 and 1:5; 1:5 and 1:10; and 1:10 and 1:25 or a range thereof. For example, the weight ratio of naloxone to second therapeutic agent may range between 1:1 and 1:5; 1:5 and 1:10; 1:10 and 1:15; or 1:15 and 1:25. Alternatively, the weight ratio of the second therapeutic agent to naloxone ranges between 2:1 and 2.5:1; 2.5:1 and 3:1; 3:1 and 3.5:1; 3.5:1 and 4:1; 4:1 and 4.5:1; 4.5:1 and 5:1; 5:1 and 10:1; and 10:1 and 25:1 or a range thereof. For example, the ratio of the second therapeutic agent to naloxone may range between 1:1 and 5:1; 5:1 and 10:1; 10:1 and 15:1; or 15:1 and 25:1.

As described above, aspects of the invention include applying to a subject a topical naloxone composition to the subject over a period of time sufficient to deliver the naloxone to the subject. In some embodiments, methods include maintaining the topical composition in contact with a subject in a manner sufficient to deliver a target dosage of the naloxone to the local skin surface of the subject, such as for example delivering a target dosage as determined by total local drug exposure or by average daily local drug exposure.

In some embodiments, topical naloxone compositions are formulated such that when applied to the skin surface of a subject the compositions exhibit trans-epidermal water loss that is less than that exhibited by a naloxone composition containing a hydrophobic delivery vehicle, such as a petrolatum. For example, topical naloxone compositions as described herein are formulated such that when applied to the skin surface of a subject the compositions exhibit trans-epidermal water loss that is less than that exhibited by a naloxone composition containing a hydrophobic delivery vehicle by 0.5 $g/m^2/hr$ or more, such as by 1 $g/m^2/hr$ or more, such as by 1.5 $g/m^2/hr$ or more, such as by 2 $g/m^2/hr$ or more, such as by 3 $g/m^2/hr$ or more, such as by 5 $g/m^2/hr$ or more, such as by 10 and including by 25 $g/m^2/hr$ or more. In some embodiments, topical naloxone compositions when applied to a skin surface of a subject exhibit a trans-epidermal water loss of 25 $g/m^2/hr$ or less, such as 20 $g/m^2/hr$ or less, such as 15 $g/m^2/hr$ or less, such as 10 $g/m^2/hr$ or less and including 5 $g/m^2/hr$ or less.

In some embodiments, methods may include maintaining the topical naloxone composition in contact with the subject in a manner sufficient to deliver a predetermined amount of naloxone to the subject. Where protocols include delivering a predetermined amount of naloxone to the subject, the locally delivered amount of naloxone may range from 0.001 mg to 2 mg, such as 0.005 to 1.9 mg, such as 0.01 mg to 1.8 mg, such as 0.05 to 1.7 mg, such as 0.1 mg to 1.6 mg, such as 0.5 mg to 1.5 mg and including from 0.5 mg to 1 mg.

In certain embodiments, the predetermined amount of naloxone delivered to the subject may be a percentage of the total amount of the naloxone present in the topical composition. For instance, the predetermined amount of naloxone locally delivered to the subject may be 1% or greater of the total amount of the naloxone present in the topical composition, such as 2% or greater, such as 5% or greater, such as 10% or greater, such as 25% or greater and including 50% or greater of the total amount of the naloxone present in the topical composition. In other words, methods may include maintaining the naloxone composition in contact with the subject in a manner sufficient to locally deliver 5% or greater of the naloxone in the topical composition to the subject over the course of a single dosage interval. For instance, where the topical composition contains 1 mg of the naloxone, methods may include maintaining the topical composition in contact with the subject in a manner sufficient to locally deliver 0.05 mg or more of naloxone to the subject over the course of the dosage interval, such as 0.1 mg or more, such as 0.25 mg or more, such as 0.4 mg or more, such as 0.45 mg or more and including 0.5 mg or more of the naloxone in the topical composition.

In certain embodiments, each of the subject methods described above may further include the step of removing the topical composition from contact with the subject at the conclusion of a dosage interval. For example, the topical composition may be removed from contact with the subject after maintaining the topical composition in contact with the subject for 0.1 hours or more, such as 0.5 hours or more, such as 1 hour or more, such as 2 hours or more, such as 4 hours or more, such as 6 hours or more, such as 8 hours or more, such as 12 hours or more, such as 16 hours or more, such as 20 hours or more and including 24 hours or more.

As described above, a dosage interval is a single administration of applying and maintaining the topical composition in contact with the subject which begins with applying the topical composition to the skin of the subject and ends with the removal of the topical composition from contact with the subject or when all of the naloxone in the composition is locally delivered to the subject. In certain embodiments, protocols may include multiple dosage intervals. In practicing methods of the invention, treatment regimens may include two or more dosage intervals, such as three or more dosage intervals, such as four or more dosage intervals, such as five or more dosage intervals, including ten or more dosage intervals.

In certain instances, a subsequent dosage interval in a treatment regimen may contain a higher or lower concentration of naloxone than the previous dosage interval. For example, the concentration of naloxone may be increased in subsequent dosage intervals by 10% or greater, such as 20% or greater, such as 50% or greater, such as 75% or greater, such as 90% or greater and including 100% or greater. An upper limit for the increase in concentration of naloxone in subsequent dosage intervals is, in some instances, 10-fold or less, such as 5-fold or less, such as 2-fold or less, such as 1-fold or less, such as 0.5-fold or less and including 0.25-fold or less.

On the other hand, the concentration of naloxone may be decreased in subsequent dosage intervals, such as by 10% or greater, such as 20% or greater, such as 50% or greater, such as 75% or greater, such as 90% or greater and including 100% or greater. An upper limit for the decrease in concentration of naloxone in subsequent dosage intervals is, in some instances, 10-fold or less, such as 5-fold or less, such as 2-fold or less, such as 1-fold or less, such as 0.5-fold or less and including 0.25-fold or less.

In other instances, a subsequent dosage interval may contain a different formulation of the naloxone free base than the previous dosage interval, such as a different types of polyethylene glycols, amount of polyethylene glycol, as described above.

In some embodiments, the skin is evaluated to assess any changes to the skin where the topical naloxone composition is applied, such as to determine the quality or color of the skin at the application site as well as whether any damage, pain, swelling or dryness has be alleviated by maintaining the topical naloxone composition in contact with the subject. In certain embodiments, the skin is evaluated to assess trans-epidermal water loss by the skin.

The site of application may be evaluated at any time during the subject methods. In some instances, the skin is evaluated while maintaining the topical composition in contact with the subject by observing or palpating the skin at regular intervals, e.g., every 0.25 hours, every 0.5 hours, every 1 hour, every 2 hours, every 4 hours, every 12 hours, every 24 hours, including every 72 hours, or some other interval. For instance, the site of application may be evaluated while maintaining the topical composition in contact with the subject, such as 15 minutes after applying the topical composition to the subject, 30 minutes after applying the topical composition, 1 hour after applying the topical composition, 2 hours after applying the topical composition, 4 hours after applying the topical composition, 8 hours after applying the topical composition, 12 hours after applying the topical composition and including 24 hours after applying the topical composition.

In other embodiments, the site of topical application is evaluated after the topical composition has been removed from contact with the subject. For example, the site of application may be evaluated 30 minutes after removing the topical composition, such as 1 hour after removing the topical composition, such as 2 hours after removing the topical composition, such as 4 hours after removing the topical composition, such as 8 hours after removing the topical composition, such as 12 hours after removing the topical composition and including 24 hours after removing the topical composition.

In some embodiments, the site where the topical composition will be applied is evaluated before the topical composition is applied to a subject, such as to record the skin color and texture before commencing a dosage interval. For example, the site of application may be evaluated 5 minutes before applying the topical composition, such as 10 minutes, such as 30 minutes, such as 60 minutes, such as 120 minutes, such as 240 minutes and including 480 minutes before applying the topical composition. Where methods include multiple dosage intervals applied sequentially, the site of application may be evaluated after each removal of the topical composition from the skin and before the subsequent topical composition dosage is applied. For example, when a first topical composition is removed, the site of application may be evaluated 2 hours, 4 hours, 6 hours, 12 hours, 24 hours, etc. after removal and before application of a second topical composition. A subsequent topical composition may be applied to the previous site of application immediately after evaluating the skin or may be applied after a predetermined time after evaluating the skin, such as 1 hours, 2 hours, 3 hours, 4 hours, 5 hours, 6 hours, 12 hours, 18 hours or 24 hours after evaluating the skin.

In some instances, the methods include assessing the severity of the condition being treated following administration of the topical composition, e.g., to determine that the composition is effective in treating the subject for the condition. As such, methods may include, following administration of the topical composition, assessing the severity the subject for a skin condition, such as an inflammatory skin disease, a non-inflammatory skin disease, pruritis or one or more symptoms associated the inflammatory skin disease, non-inflammatory skin disease or pruritis. For example, methods in some instances include assessing the severity of an inflammatory skin disease, such as atopic dermatitis, eczema, psoriasis, or a combination thereof. In other instances, methods include assessing the severity of a non-inflammatory skin disease, such chronic prurigo. In yet other instances, methods include assessing the severity of pruritus. In certain instances, the pruritis is pruritis associated with one or more of primary biliary cirrhosis, chronic renal failure, renal dialysis, abnormal blood pressure, thyroid gland malfunction, aging, cancer, anemia, a parasite, a neurological condition or pregnancy. In certain embodiments, the pruritus is a drug-induced pruritus or a pruritogen-induced pruritus. In certain embodiments, the pruritis is associated with a condition selected from shingles, psoriasis, hives, notalgia paresthetica, Grover's disease, chronic kidney disease and Hailey-Hailey disease. The pruritus may be accompanied by skin redness, skin bumps, spots or blisters, dry or cracked skin, leathery skin or scaly textured skin and methods may also include applying an amount of the subject naloxone composition sufficient to treat one or more of the skin redness, skin bumps, spots or blisters, dry or cracked skin, leathery skin or scaly textured skin that accompanies the pruritus.

Kits

Kits for use in practicing certain methods described herein are also provided. In certain embodiments, the kits include one or more topical naloxone compositions, e.g., as described above. In certain embodiments, the kits include a dispensing device, such as a dropper or a metered dispenser. In some instances, the topical naloxone composition is present in a squeezable tube, such as a squeezable tube configured for holding an ointment. Kits may also include an applicator such as a sponge, brush, doctor blade, spreading device, smoothing device or a combination thereof. In certain embodiments, kits further include an overlay, such as a waterproof adhesive overlay that can be used to cover the site of application of the topical composition.

In a given kit that includes two or more of the subject topical compositions, the compositions may be individually packaged or present within a common container. In certain embodiments, the kits will further include instructions for practicing the subject methods or means for obtaining the same (e.g., a website URL directing the user to a webpage which provides the instructions), where these instructions may be printed on a substrate, where substrate may be one or more of: a package insert, the packaging, reagent containers and the like. In the subject kits, the one or more components are present in the same or different containers, as may be convenient or desirable.

The following example(s) is/are offered by way of illustration and not by way of limitation

EXPERIMENTAL

A. Detection of Degradation Product

Formulations further detailed below were prepared by adding and stirring all components (e.g., low MW PEGs, NLX, and other additives, such as antioxidants, glycerol, citric acid, etc.) except PEG1450 at room temperature first. Then PEG1450 was added and heated to about 50° C. until all the PEG1450 was melted. Once a homogeneous mixture was formed, it was filled into tubes (one inch laminate tubes with 0.305 inch orifice from Albea), and sealed with foil. The inner layer of the laminate was Linear Low Density Polyethylene (LLDPE). The filled tube was allowed to cool to room temperature to form an opaque ointment inside the tube.

Stability studies of PEG-based naloxone ointment formulations were performed at 25, 40 and 60 degrees Celsius. The formation of one particular degradation product (also referred to as "related substance") was consistently observed at each of these temperature conditions. This related substance typically appeared within one-week of making the formulation. Primarily using HPLC, we found that increased temperature and humidity further increased the quantity of the degradation product relative to naloxone. This related substance was found to be forming at significantly high levels and also consistently appeared when using a variety of excipients and storage conditions. Over time it appears as though a small percentage of the naloxone degrades chemically by an oxidative process to produce a related substance (relative retention time (RRT) by HPLC of 0.79). The impurity at RRT 0.79 was an unknown related substance.

Naloxone HCl was also found to be unstable in PEG-based formulations. A 9.1% solution of naloxone HCl in water was made. A PEG-based formulation was prepared by combining 1.00 g of this aqueous 9.1% naloxone HCl solution with 4.70 g of PEG 300 and 4.30 g of PEG 1450 for a total weight of 10.00 g of this 0.91% Naloxone HCl. The stability at room temperature of this naloxone HCl formulation was assessed by HPLC over 2 months. In the second month there was a large increase in the growth of degradation products as shown in Table 1, below. This indicates that naloxone HCl is also unstable in this PEG=based formulation. Deg 1 matches the relative retention time of the aforementioned unknown related substance.

TABLE 1

|  | NLX, Area | Deg 1, RT | Deg 1 % | Deg 2, RT | Deg 2 % | Deg 3, RT | Deg 3 % |
|---|---|---|---|---|---|---|---|
| t = 0 | 2242.76 | 0.00 | 0.00 | 0.00 | 0.00 | 0.00 | 0.00 |
| t = 1 wk | 2250.68 | 8.08 | 0.22 | 0.00 | 0.00 | 0.00 | 0.00 |
| t = 2 wks | 2250.09 | 7.94 | 0.34 | 3.48 | 0.06 | 0.00 | 0.00 |
| t = 3 wks | 2084.89 | 7.78 | 0.47 | 3.45 | 0.12 | 0.00 | 0.00 |
| t = 1 mo | 2100.74 | 7.60 | 0.62 | 3.43 | 0.13 | 0.00 | 0.00 |
| t = 2 mo | 2255.99 | 7.62 | 1.08 | 3.42 | 0.31 | 3.66 | 0.15 |

B. Isolation and Identification of Naloxone N-Oxide

The unknown related substance was isolated using a multi-step liquid chromatography process that took considerable time and effort due to the large quantities of PEG material that needed to be separated to identify the degradation product of interest. Approximately 200 g of 1% naloxone free base ointment in PEG300 were aged in a humidity chamber and used for the isolation. The degradation product of interest was enriched in the formulation sample by C18 cartridge washing with 6.2 mM aqueous 1-octanesulfonate sodium salt with 0.1% phosphoric acid, and then eluting with a 40% methanol solution. Fractions containing the related substance were combined and lyophilized. The degradant was isolated by prep HPLC using a Shimadzu Prominence Preparative HPLC system. A Phenomenex Luna C18 column (5 μm, 21.2×150 mm) with a Security Guard PREP C18 cartridge (21.2×15 mm) was used.

A 35% methanol in 6.2 mM aqueous 1-octansulfonate sodium salt with 0.1% phosphoric acid mobile phase was used. The flow rate was 20 mL/min for an 18 minutes isocratic run. The UV detector wavelength was 205 nm. Fractions were collected between 7 and 14 minutes when a slope of 100 uV/sec and level of 50,000 uV were observed. Re-analysis of the fractions with analytical HPLC showed the related substance presented in the fraction samples had >99% purity (Appendix A23). An Agilent Zorbax Eclipse XDB-C18 (5 μm, 4.6×150 mm) analytical column running an isocratic 35% methanol in 6.2 mM aqueous 1-octanesulfonate sodium salt with 0.1% phosphoric acid mobile phase over 15 minutes was used for analytical purity. Final isolation of the impurity was complete upon removal of the buffer using a strong cation exchange (SCX) cartridge washing with methanol and then eluting with 5% HCl in water. Fractions containing the related substance were combined and pH adjusted to 7.0±0.5. The degradant was extracted four times with an equivalent amount of a 3:1 solution of chloroform and isopropanol. Combined organic extractions were dried over sodium sulfate and concentrated to dryness. After purification on the SCX cartridge the purity of the isolated degradant dropped to 92%.

Once a sufficient amount of milligrams of the degradation product had been isolated, it was characterized using mass-spectrometry and NMR. High resolution mass spectrometry data of the isolated degradant was acquired using a Waters UPLC Xevo G2-XS QT of system controlled by Waters UNIFI software. A Waters CORTECS UPLC Shield RP18 (1.6 μm 3×50 mm) column was used. Mobile phase A was 0.1% formic acid in water and mobile phase B was 0.1% formic acid acetonitrile. The flow rate was 0.2 mL/min. A gradient of 5%-90% B in 5 minutes was applied. HRMS gave a molecular formula of C19H21NO5 with a mass error of less than 5 ppm.

NMR data were acquired on a Bruker 400 MHz spectrometer at ambient temperature. Chemical shifts were reported in ppm relative to TMS.NMR experiments were performed using $^1$H, $^{13}$C and also $^{15}$N nuclei, as well as two-dimensional NMR experiments. The observed signals in the acquired 1H NMR spectrum are in agreement with expected number of protons and types of protons for the proposed structure. Analysis of the $^{13}$C NMR spectrum showed 18 resonances of 19 carbons. Carbons assignments were done using data available from all NMR experiments. The obtained $^{15}$N NMR spectrum showed 1 resonance of 1 nitrogen at 129.2 ppm. The observed $^{15}$N shift supports the assignment of the proposed structure as the N-oxide. The NMR data confirms that the naloxone core structure is intact and that there is no loss of proton or carbons signals. Importantly, 21 protons, 5 CH carbons, and 7 CH2 carbons were observed, indicating that the additional identified oxygen from mass spec data is not bonded to any carbon atoms. Compared to naloxone, there were significant shifts downfield observed for the 2 exchangeable protons as well as the signals assigned to H9, H16, H17, and H10. Nitrogen NMR results showed a significant shift from 41.5 ppm (naloxone) to 129.2 ppm (degradant). These data showed a significant change in the electrons around the nitrogen atom for the impurity. With the MS data it was concluded that the impurity is naloxone N-oxide. Finally, the isolated related substance was directly compared by HPLC to a commercially available standard of naloxone N-oxide. The amount of naloxone N-oxide is first determined by the naloxone standard and then corrected for the response factor. The response factor for naloxone N-oxide is 1.19.

Comparison of Naloxone and Naloxone N-Oxide Structures:

Structures of Naloxone and the Isolated Impurity, Naloxone N-oxide.

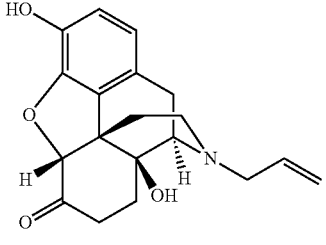

Naloxone
Chemical Formula: C19H21NO4
Exact Mass: 327.15

-continued

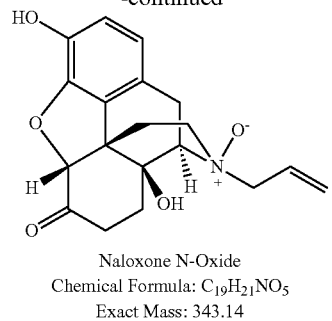

Naloxone N-Oxide
Chemical Formula: C19H21NO5
Exact Mass: 343.14

C. Forced Degradation Studies of Naloxone

The forced degradation of 0.5% naloxone drug substance (Siegfried, Batch 1530F001) was studied as a control in the presence of either 5N hydrochloric acid, 5N sodium hydroxide, or 3% hydrogen peroxide for 18 hours or at 60° C. for 2 weeks. With the exception of the hydrogen peroxide treatment, the total related substances detected for the control and the other treatments were below 1% by peak areas relative to total area. In contrast, with the 3% hydrogen peroxide after 18 hours 3 degradation products were observed: 1.75% at 0.66 RRT; 1.59% at 0.72 RRT, and 20.42% at 0.94 RRT. The peak at 0.72 corresponded to the related substances peak at 0.79 RRT, which was identified as naloxone N-oxide. The peak at 0.94 RRT co-eluted with the naloxone peak. This forced degradation clearly demonstrates the reactivity of naloxone with peroxides and potential for degradation due to oxidation compared to other stresses.

D. Summary of Attempts to Stabilize PEG-Based Naloxone Ointment

The major issue encountered during formulation development of the PEG-based naloxone ointment is chemical instability due to the interaction between naloxone and PEG due to oxidation. To address this stability issue, several different approaches have been investigated including:

The use of antioxidants (Citric acid, BHT, tocopherol, and sodium metabisulfite)

Manufacture processing and storage control with inert gas (argon gas or nitrogen gas)

Use of different PEGs (PEG 300 vs. PEG 400)

Use of different sources of PEGs (PEGs from Dow, Croda, BASF, EMD Millipore, and Clariant)

In summary, the formulations with the best stability can be obtained through the following essential approaches:
1. Use Croda's super refined PEG 400 from an unopened container
2. Implement argon protection during the mixing process
3. Bubble argon through the melted ointment before filling
4. Use an argon blanket in the tube or container headspace to keep ointment from any contact with air 1. Formulations with Antioxidants Formulations were prepared by adding and stirring all components except PEG1450 at room temperature first. Then PEG1450 was added and heated to about 50° C. until all the PEG1450 was melted. Once a homogeneous mixture was formed, it was filled into tubes and capped, where it was allowed to cool to room temperature to form an opaque ointment. Tocopherol and/or citric acid were added as antioxidants to 1% PEG-based naloxone (NLX) ointments. Both PEG 300 and PEG 400 were examined for differences in stability at 25° C. over 3 months, and the results are shown in Table 2, below.

TABLE 2

| Lot# | Formulation | 25° C. Naloxone N-oxide Degradant % | | | |
|---|---|---|---|---|---|
| | | 0 | 1 mo | 2 mo | 3 mo |
| 45-80-1 | 1% NLX<br>56% PEG 300<br>43% PEG 1450<br>0.30% alpha-tocopherol | 0.23 | 0.66 | 0.76 | 0.85 |
| 45-80-4 | 1% NLX<br>56% PEG 300<br>43% PEG 1450<br>0.20% alpha-tocopherol | 0.48 | 1.45 | 1.55 | 1.58 |
| 45-80-6 | 1% NLX<br>56% PEG 300<br>43% PEG 1450<br>0.10% alpha-tocopherol | 0.48 | 1.29 | 1.42 | 1.52 |
| 45-81-3 | 1% NLX<br>56% PEG 300<br>43% PEG 1450<br>0.40% alpha-tocopherol | 0.56 | 2.55 | 2.89 | 3.27 |
| 209-26-1 | 1% NLX<br>18% Glycerin<br>36% PEG 300<br>43% PEG 1450<br>2% Citric Acid | 0.00 | 0.29 | 0.31 | 1.08 |
| 209-26-2 | 1% NLX<br>19% Glycerin<br>36% PEG 300<br>43% PEG 1450<br>1% Citric Acid | 0.00 | 0.52 | 1.08 | 1.52 |
| 209-26-3 | 1% NLX<br>55% PEG 300<br>42% PEG 1450<br>2% Citric Acid | 0.00 | 0.85 | 1.73 | 2.16 |
| 209-26-4 | 1% NLX<br>55% PEG 300<br>42% PEG 1450<br>2% Citric Acid<br>KOH+Sieve | 0.00 | 1.04 | 1.68 | 1.92 |
| 209-40-4 | 1% NLX<br>53% PEG 300<br>43% PEG 1450<br>1% Citric Acid<br>1% Tocopherol | 0.00 | 1.61 | 2.42 | 3.00 |
| 209-49-6 | 1% NLX<br>52.5% PEG 300<br>43% PEG 1450<br>0.5% Citric Acid<br>3% Tocopherol | 0.00 | 1.97 | 3.36 | 4.19 |
| 209-49-7 | 1% NLX<br>52.5% PEG 400<br>43% PEG 1450<br>0.5% Citric Acid<br>3% Tocopherol | 0.00 | 0.30 | 0.66 | 0.96 |
| 209-49-8 | 1% NLX<br>20% Glycerin<br>32.5% PEG 300<br>43% PEG 1450<br>0.5% Citric Acid<br>3% Tocopherol | 0.00 | 2.26 | 3.51 | 4.37 |
| 209-49-9 | 1% NLX<br>53% PEG 300<br>43% PEG 1450<br>3% Tocopherol | 0.00 | 3.44 | 5.23 | 6.25 |
| 209-54-3 | 1% NLX<br>60.5% PEG 400<br>35% PEG 1450<br>0.5% Citric Acid<br>3% Tocopherol | 0.00 | 0.56 | 1.14 | 1.49 |
| 209-54-4 | 1% NLX<br>20% Glycerin<br>40.5% PEG 400<br>35% PEG 1450<br>0.5% Citric Acid<br>3% Tocopherol | 0.00 | 0.84 | 1.30 | 1.60 |

While some differences were observed among formulations, none of the added antioxidants, or changes in the PEG used, stabilized the ointment to reduce the naloxone N-oxide to a sufficiently low (near zero) level. An additional study of other formulations was performed at shorter time points and the results are shown in Table 3, below.

TABLE 3

| Lot# | Formulation | 25° C. Naloxone N-oxide Degradant % | | | |
|---|---|---|---|---|---|
| | | 0 | 1 wk | 3 wk | 6 wk |
| 209-44-2 | 1% NLX<br>53% PEG 300<br>43% PEG 1450<br>1% Citric Acid<br>2% Tocopherol | 0.00 | 0.29 | 1.07 | 1.73 |
| 209-44-3 | 1% NLX<br>20% Glycerin<br>36% PEG 300<br>43% PEG 1450<br>2% Tocopherol | 0.86 | 2.84 | 3.76 | 4.03 |
| 209-44-4 | 1% NLX<br>20% Glycerin<br>33% PEG 300<br>43% PEG 1450<br>1% Citric Acid<br>1% Tocopherol | 0.00 | 0.17 | 0.64 | 1.10 |
| 209-44-5 | 1% NLX<br>20% Glycerin<br>35% PEG 300<br>43% PEG 1450<br>0.5% Citric Acid<br>0.5% Tocopherol | 0.00 | 0.82 | 1.04 | 2.95 |
| 209-44-6 | 1% NLX<br>20% Glycerin<br>32% PEG 300<br>43% PEG 1450<br>1% Citric Acid<br>3% Tocopherol | 0.00 | 0.17 | 0.62 | 1.09 |

Again, the added antioxidants did not sufficiently stabilize the naloxone in the ointments to a near zero level of naloxone N-oxide.

2. Use of Low Molecular Weight PEG's with Very Low Peroxide Values

1% (w/w) Naloxone base ointments were prepared with PEG300 or PEG400 from different sources (Dow, Croda, BASF, EMD Millipore, and Clariant). The PEGS from different sources were examined for initial peroxide value of the low molecular weight PEG used and for stability of the naloxone as reflected by the growth of the naloxone N-oxide degradant. These ointments were prepared using the following essential processes:

1. Use PEG 300 or PEG 400 from an unopened container
2. Implement argon protection during the mixing process
3. Bubble argon through the melted ointment before filling
4. Use an argon blanket in the tube or container headspace to keep ointment from any contact with air The following 1% naloxone ointments were prepared, as summarized in Table 4, below:

TABLE 4

| Formulation No. | Formulation (% w) | Source of Low MW PEG | Peroxide Value of Low MW PEG (ppm) |
|---|---|---|---|
| 209-83-1 | 57% PEG 300 42% PEG 1450 | EMD Millipore | 3.14 |
| 45-80-2 | 56% PEG 300 43% PEG 1450 | BASF | 30.3 |
| 179-149-2 | 60% PEG 400 39% PEG 1450 | Croda super refined | 11.99 |
| 209-81-2 | 65% PEG 400 34% PEG 1450 | Dow purified | 28.79 |
| 209-68-6 | 60% PEG 400 39% PEG 1450 | Dow | 101.39 |

Figure 2:
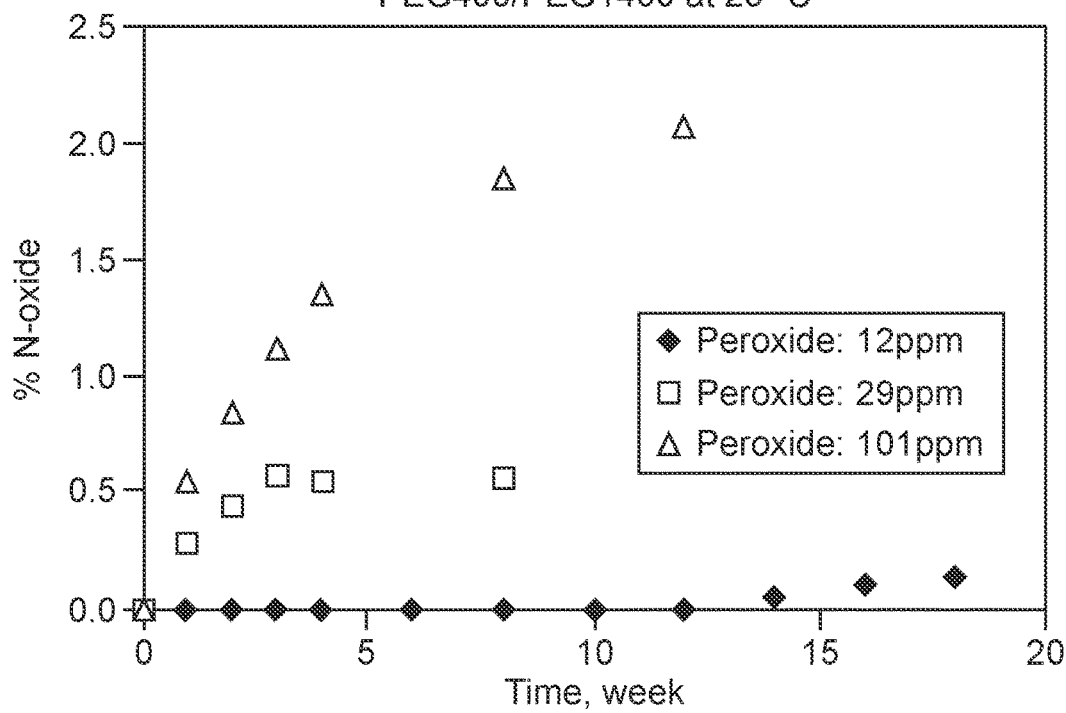

The percentages of naloxone N-oxide for each of these ointments are shown in FIGS. 1 and 2, and the ointments prepared from either PEG 300 or PEG 400 containing 12 ppm or below of peroxides exhibit negligible and pharmaceutically acceptable levels of naloxone N-oxide while those prepared with low molecular weight PEG's with greater levels of peroxide, even the purified PEG 400 obtained from Dow, exhibited unacceptable growth of this identified degradant with time.

Table 5 below shows the stability data for a 1% naltrexone base (w/w) formulation prepared with Croda super refined PEG 400 (1% API, 60% PEG 400, 39% PEG 1450). The response factor of 1.19 was used to calculate the level of degradant naloxone N-oxide. For other unknown related substances, the response factor is assumed to be one. These data in the Table below demonstrate that in terms of these assays, this formulation prepared with a low peroxide PEG 400 source and the previously described method is acceptable stability over 2 years at room temperature based on 6 months, 40° C./75% RH data.

TABLE 5

| Time, | Assay, % | | Known Impurity-Naloxone N-oxide, % | | Unknown Related Substance-1, % | | Unknown Related Substance-2, % | |
|---|---|---|---|---|---|---|---|---|
| week | 25° C. | 40° C. | 25° C. | 40° C. | 25° C. | 40° C. | 25° C. | 40° C. |
| 0 | 100.00 | 100.00 | 0.00 | 0.00 | 0.00 | 0.00 | 0.00 | 0.00 |
| 1 | 100.50 | 100.39 | 0.00 | 0.00 | 0.00 | 0.00 | 0.00 | 0.00 |
| 2 | 100.03 | 99.91 | 0.00 | 0.05 | 0.00 | 0.00 | 0.00 | 0.00 |
| 3 | 99.69 | 100.27 | 0.00 | 0.06 | 0.00 | 0.00 | 0.00 | 0.00 |
| 4 | 100.70 | 100.77 | 0.00 | 0.10 | 0.00 | 0.00 | 0.00 | 0.00 |
| 6 | 101.68 | 99.74 | 0.00 | 0.14 | 0.00 | 0.00 | 0.00 | 0.00 |
| 8 | 101.70 | 99.16 | 0.00 | 0.10 | 0.00 | 0.00 | 0.00 | 0.00 |
| 10 | 101.03 | 98.73 | 0.00 | 0.07 | 0.00 | 0.08 | 0.00 | 0.00 |
| 12 | 101.16 | 98.28 | 0.00 | 0.09 | 0.00 | 0.10 | 0.00 | 0.00 |
| 14 | 102.19 | 97.99 | 0.04 | 0.10 | 0.00 | 0.08 | 0.00 | 0.10 |
| 16 | 101.39 | 97.08 | 0.09 | 0.05 | 0.00 | 0.10 | 0.00 | 0.00 |
| 18 | 101.77 | 97.78 | 0.12 | 0.04 | 0.00 | 0.12 | 0.00 | 0.00 |
| 24 | 102.26 | 98.37 | 0.12 | 0.19 | 0.00 | 0.13 | 0.00 | 0.00 |

3. Minimal Effect of Argon in Processing and Storage

A 1.0% naloxone free base (NLX) PEG-based ointment was prepared with Croda super refined (low peroxides) PEG 400 (60%) and PEG1450 (39%) with and without argon bubbling through the melted ointment and blanketing the tube. This same formulation was also prepared with PEG 400 that was not low in peroxides and with the added argon processing. In an accelerated stability study at 40° C./75% RH for 6 months, low peroxide PEG 400 (SR) formulations both with and without argon processing exhibited low concentrations of degradant 1 (naloxone N-oxide) while the higher peroxide PEG 400 formulations had greater concentrations of this degradant (see Table 6 below). Note at longer times for the higher peroxide PEG400 (Hi) formulation, this effect is actually partially obscured by the naloxone N-oxide further degrading to other degradants. The argon processing has no clear improvement in the rate of degradation while the level of peroxides in the PEG 400 sourced has a profound effect.

TABLE 6

| Time | Hi PEG + Ar Deg 1 % | SR PEG + Ar Deg 1% | SR PEG − Ar Deg 1 % |
|---|---|---|---|
| t = 1 wk | 0.69 | 0.00 | 0.00 |
| t = 2 wks | 0.89 | 0.00 | 0.00 |
| t = 3 wks | 1.12 | 0.28 | 0.31 |
| t = 1 mo | 0.92 | 0.35 | 0.41 |
| t = 6 wks | 0.84 | 0.43 | 0.46 |
| t = 2 mo | 0.71 | 0.19 | 0.24 |
| t = 10 wks | 0.63 | 0.20 | 0.22 |
| t = 3 mo | 0.50 | 0.16 | 0.19 |
| t = 5 mo | 0.47 | 0.29 | 0.35 |
| t = 6 mo | 0.39 | 0.24 | 0.29 |

E. Identification of Additional Impurities

1. Gradient Assay Method

In the HPLC method used for the prior studies ("Old" Method) it was suspected that another impurity that co-eluted with N-oxide. A "New" gradient method with a longer run time was developed to provide quantitation of this potentially new impurity. In addition, the "Old" method has a sample concentration of 100 μg/mL which leads to a greater limit of quantitation (LOQ) and limit of detection (LOD). The "New" method provided more sensitivity by increasing the sample concentration to 500 μg/mL. The LOQ for the "new" impurity method is about 0.03% while the LOD is 0.02%. The "Old" impurity method was simultaneously utilized as the assay method for comparison. The "New" method is used in the following examples.

TABLE 7

Comparison of "Old" and "New" Impurity Method

| Parameter | "Old" Method | "New" Method |
|---|---|---|
| Column | C18, 4.6 × 150 mm, 5 μm | C18, 4.6 × 150 mm, 5 μm |
| Injection Volume | 10 μL | 20 μL |
| Flow Rate | 1.00 mL/min | 0.300 mL/min |
| Mobile Phase | MeOH/6.3 mM $CH_3(CH_2)_7SO_3Na$ + 0.1% $H_3PO_4$ (35/65, v/v) | MeOH/18.9 mM $CH_3(CH_2)_7SO_3Na$ + 0.1% $H_3PO_4$ (35/65, v/v) |
| Run Time | 15 min | 65 min |
| Gradient? | NO | YES |

TABLE 8

Gradient of Flow Rate for New Impurity Method

| Time (min) | Flow Rate (mL/min) |
|---|---|
| 0.0 | 0.300 |
| 20.0 | 1.000 |
| 60.0 | 1.000 |
| 60.1 | 0.300 |
| 65.0 | 0.300 |

2. Effect of High Molecular Weight PEG

A 1.0% naloxone free base (NLX) PEG-based ointment was prepared with Croda super refined (low peroxides) PEG 400 (60%) and PEG1450 (39%) from 2 different manufacturers (Dow and BASF). Both ointments were prepared with flooding with argon. In Table 9, it is clear that the growth of the impurities at these 5 RRT was consistently greater in the DOW PEG1450, particularly when stored at 40° C. In other words, the use of the BASF PEG1450 with the Croda PEG 400 was more stable.

3. Effect of Anti-Oxidant for Formulation with BASF PEG1450

This same more stable formulation, i.e., BASF PEG1450 with the Croda PEG 400, was also prepared with the addition of selected anti-oxidants, BHT and propyl gallate, both of which were soluble in polyethylene glycol.

Changes were made in this set of experiments as follows. First, storage at the 60° C. condition was replaced storage at a 40° C. condition. A 40° C. condition is not a typical accelerated stability condition for this PEG ointment, because below 40° C. the composition may contain both liquid and solid components while at 40° C. the ointment is liquid, i.e. there is a phase transition to liquid, and even 40° C. represents a more extreme challenge to stability than just a temperature excursion. Storage at 60° C. is similar to a forced degradation condition and can be considered as the worst-case scenario. Under 60° C., the ointment is fully in liquid form. One month at 60° C. is considered approximately 2 years at 25° C. Since this extreme temperature may allow different pathways of degradation, some degradation that could occur at 60° C. may never happen at lower temperatures. Second, the assay is reported in this study as % of total ointment. The targeted API loading is 1%.

While antioxidants have been used in the past for formulation with Dow PEGs, the impurity concentrations were too high in Dow PEG formulations that the effect of antioxidants were not observed. With Croda super-refined PEG 400 and BASF PEG 1450, the overall impurity level is much lower when compared to prior formulations. In the present case, with Croda PEG 400 and BASF PEG 1450, the use of selected antioxidants appears beneficial. Tables 10 and 11 compare the formulation with Croda PEG 400 and BASF PEG 1450 with and without antioxidants, 1% propyl gallate and 0.1% BHT. Lot 209-132-1 is similar to lot 209-115-1 from Table 9, except it contains BASF PEG 1450. Specifically, we have found that the formulation with 0.1% BHT in Table 10 does not have any impurity above 0.2% after one month at 60° C., while the formulation with 1% propyl gallate is also more stable than the same formulation without an antioxidant.

TABLE 9

Stability data on selected impurities for BASF vs. Dow PEG 1450 comparison

| RRT/temperature | 25° C. | | | | | 40° C. | | | | |
|---|---|---|---|---|---|---|---|---|---|---|
| Sample/time point | 0.32 | 0.43 | 0.82 | 0.86 | 2.63 | 0.32 | 0.43 | 0.82 | 0.86 | 2.63 |
| Lot 209-115-1 (BASF PEG1450, with argon) | | | | | | | | | | |
| 1 month | — | 0.14 | 0.15 | 0.08 | — | 0.05 | 0.14 | 0.09 | 0.09 | 0.09 |
| 2 months | — | 0.16 | 0.22 | 0.10 | — | 0.07 | 0.16 | 0.10 | 0.12 | 0.24 |
| 3 months | 0.05 | 0.18 | 0.22 | 0.10 | 0.05 | 0.09 | 0.19 | 0.08 | 0.14 | 0.34 |
| 6 months | | | | | | | | | | |
| Lot 209-95-2 (Dow PEG1450, with Argon) | | | | | | | | | | |
| 1 month | — | 0.08 | 0.08 | 0.06 | — | 0.17 | 0.25 | 0.26 | 0.17 | 0.18 |
| 2 months | 0.07 | 0.12 | 0.22 | 0.12 | — | 0.22 | 0.25 | 0.22 | 0.19 | 0.45 |
| 3 months | 0.10 | 0.27 | 0.41 | 0.22 | — | 0.27 | 0.34 | 0.17 | 0.22 | 0.73 |
| 6 months | 0.13 | 0.24 | 0.44 | 0.20 | — | 0.30 | 0.22 | 0.10 | 0.21 | 1.08 |

TABLE 10

Stability data on selected impurities for BASF formulation and anti-oxidant

| RRT/temperature | 25° C. | | | | | 40° C. | | | | |
|---|---|---|---|---|---|---|---|---|---|---|
| Sample/time point | 0.32 | 0.43 | 0.82 | 0.86 | 2.63 | 0.32 | 0.43 | 0.82 | 0.86 | 2.63 |
| Lot 209-132-1 (BASF PEG1450), with argon | | | | | | | | | | |
| 1 week | — | — | — | — | — | — | 0.10 | 0.09 | — | 0.99 |
| 2 week | — | — | — | — | — | 0.07 | 0.13 | 0.14 | 0.20 | 0.99 |
| 1 month | — | 0.10 | 0.07 | — | 1.00 | 0.12 | 0.14 | 0.21 | 0.45 | 0.98 |
| Lot 209-132-2 (Dow PEG1450, 1% propyl gallate), with argon | | | | | | | | | | |
| 1 week | — | — | — | — | — | — | — | — | — | 1.00 |
| 2 week | — | — | — | — | — | — | — | — | — | 1.01 |
| 1 month | — | — | — | — | 1.00 | 0.11 | — | 0.12 | 0.31 | 1.00 |
| Lot 209-132-3 (BASF PEG1450, 0.1% BHT), with argon | | | | | | | | | | |
| 1 week | — | — | — | — | — | — | — | — | — | 1.00 |
| 2 week | — | — | — | — | — | — | — | — | — | 1.00 |
| 1 month | — | — | — | — | 0.99 | — | 0.07 | 0.06 | 0.19 | 1.00 |

Note:
1. The unit of number is % for impurity and % of API loading for assay
2. "—" means "not detected".

A 30° C. storage condition was also used as a less severe accelerated condition in which there was no phase transition to a liquid. Even after 3 months at 30° C., the same trend is observed that the formulation without antioxidant was less stable, the propyl gallate formulation was more stable, and the BHT formulation was the most stable.

TABLE 11

Stability data on selected impurities for same BASF formulations and anti-oxidants

| | RRT/temperature 30° C. | | | | |
|---|---|---|---|---|---|
| Sample/time point | 0.32 | 0.43 | 0.87 | 2.36 | Assay |
| Lot 209-132-1 (BASF PEG1450), with argon | | | | | |
| 1 month | — | — | 0.07 | — | 1.01 |
| 3 months | — | — | 0.09 | — | 1.01 |
| Lot 209-132-2 (BASF PEG1450, 1% propyl gallate), with argon | | | | | |
| 1 month | — | — | — | — | 1.00 |
| 3 months | — | — | — | — | 0.97 |
| Lot 209-132-3 (BASF PEG1450, 0.1% BHT), with argon | | | | | |
| 1 month | — | — | — | — | 0.99 |
| 3 months | — | — | — | — | 1.00 |

To determine the effect of BHT concentration on the stability of naloxone in this Croda PEG 400/BASF PEG 1450, the stability was studied at 40° C. and exhibited improved stability even at 0.02% BHT.

TABLE 12

Stability data on selected impurities for BASF PEG 1450 formulations with varying concentrations of BHT at 40° C.

| | RRT at 40° C. | | | | |
|---|---|---|---|---|---|
| Sample/time point | 0.32 | 0.46 | 0.87 | 2.43 | Assay |
| Lot 209-139-6 (BASF PEG 1450), no BHT | | | | | |
| 1 month | 0.11 | 0.11 | 0.08 | 0.06 | 0.98 |
| Lot 209-139-5 (BASF PEG 1450), 0.02% BHT | | | | | |
| 1 month | 0.06 | — | — | — | 0.99 |
| Lot 209-139-4 (BASF PEG 1450), 0.05% BHT | | | | | |
| 1 month | 0.05 | — | — | — | 0.99 |
| Lot 209-139-3 (BASF PEG 1450), 0.1% BHT | | | | | |
| 1 month | 0.05 | — | — | — | 0.99 |
| Lot 209-139-7 (BASF PEG 1450), 0.1% BHT | | | | | |
| 1 month | — | — | — | — | 0.99 |

A third source of a close molecular weight to PEG1450, JP Macrogol 1500R, was also investigated (Table 6) and found to show improved stability with antioxidants and better than Dow PEG1450, but not as good as BASF PEG 1450.

TABLE 13

Stability data on selected impurities for JP Macrogol 1500R formulations at 40° C.

| | RRT at 40° C. | | | | | |
|---|---|---|---|---|---|---|
| Sample/time point | 0.3 | 0.41 | 0.81 | 0.85 | 2.79 | Assay |
| Lot 209-141-3 (39% Macrogol 1500R), no BHT | | | | | | |
| 1 month | 0.58 | 0.64 | 1.3 | 0.44 | 1.15 | 0.96 |
| Lot 209-141-2 (39% Macrogol 1500R), 0.1% BHT | | | | | | |
| 1 month | — | — | 0.5 | — | 0.46 | 1.01 |
| Lot 209-141-4 (34% Macrogol 1500R ), 0.1% BHT | | | | | | |
| 1 month | — | — | 0.47 | — | 0.43 | 1.01 |

Additional examples with antioxidants are shown in the tables below, and in addition to the confirming the aforementioned results of improvement with BHT and propyl gallate, demonstrate that propyl gallate did improve stability even at 0.1% propyl gallate. Data were collected on this same Croda PEG 400/BASF PEG 1450 that compared 0.05% propyl gallate versus 0.1% BHT, and at 3 months at 60° C. the level of impurity at RRT 0.81 was 0.05 and 0.06, respectively. Levels as low as 0.05% propyl gallate or 0.02% BHT in combination with the use of BASF PEG 1450 provided improved stability of the ointment.

TABLE 14

60° C. data for BASF PEG 1450 with anti-oxidant

| Sample/time point | RRT | |
|---|---|---|
| | 0.88 | 2.22 |
| Lot 209-136-1 (BASF PEG1450, 0.1% BHT) | | |
| 1 week | — | — |
| 2 week | — | — |
| 1 month | 0.06 | 0.19 |
| Lot 209-136-7 (BASF PEG 1450, 0.1% propyl gallate) | | |
| 1 week | — | — |
| 2 week | — | — |
| 1 month | 0.07 | 0.18 |
| Lot 209-136-8 (BASF PEG1450, 1% BHT) | | |
| 1 week | — | — |
| 2 week | — | — |
| 1 month | 0.18 | 0.37 |

TABLE 15

| Sample/time point | RRT-40 C. | | RRT-60 C. | |
|---|---|---|---|---|
| | 0.87 | 2.43 | 0.87 | 2.43 |
| Lot 209-139-3 (BASF PEG1450, 0.1% BHT) | | | | |
| 1 week | — | — | — | 0.05 |
| 2 week | — | — | — | 0.1 |
| 1 month | — | 0.06 | 0.06 | 0.24 |

F. Efficacy of Naloxone Ointment in a Rat Model of Atopic Dermatitis Pruritis

Atopic dermatitis skin symptoms were induced by providing a special feed diet 10 to mice (HOS:HR-1 hairless). All groups were treated with daily 0.1 ml/day of ointment over the entire back of each mouse for three consecutive weeks starting on Day 34. Mice were video recorded pre-dose (baseline activity) for 30 minutes and observed for scratching for a period of one hour post application on days 34, 35, 38, 41, 45, 48, and 55. The topical naloxone active agent composition was allowed to dry 15 for one (1) hour prior to video recording of scratching behavior. Scratching behavior was monitored every 5 minutes for an hour where the number of scratching bouts includes one or more of the following actions: hind leg raised, scratching the back or lowering the leg to the floor. Cumulative duration of scratching behavior was also determined. Trans-epidermal water loss (TEWL) measured on Days 34, 48, 55 20 (Phase 2) and Days 33 and 55 (Phase 3) was also measured. Formulations for treatment according to groups is shown in Table 16, below.

TABLE 16

| Phase | Group | Dosage (mL) | Topical Composition | Percent Naloxone w/w |
|---|---|---|---|---|
| 2 & 3 | Control | 0.1 | No Treatment | 0.0 |
| 2 | Active 1 | 0.1 | 55% of PEG300 with Naloxone base + 45% PEG1450 | 4.07 |
| 2 | Placebo 1 | 0.1 | 55% of PEG300 + 45% PEG1450 | 0.0 |
| 2 | Active 2 | 0.1 | 11.2% of PEG300 with Naloxone base + 88.8% SheaXP | 0.83 |
| 2 | Placebo 2 | 0.1 | 11.2% of PEG300 with Naloxone base + 88.8% SheaXP | 0.0 |
| 3 | Active 4 | 0.1 | 10% of PEG:Water (50:50) with Naloxone HCl + 90% Shea XP | 0.85 |
| 3 | Placebo 4 | 0.1 | 5% PEG300 + 5% Water + 90% Shea XP | 0.0 |
| 3 | Active 5 | 0.1 | 55% of PEG300 + 39.5% PEG 1450 with Naloxone HCl | 5.0 |
| 3 | Placebo 5 | 0.1 | 55% of PEG300 + 45% PEG 1450 | 0.0 |

Figure 4:
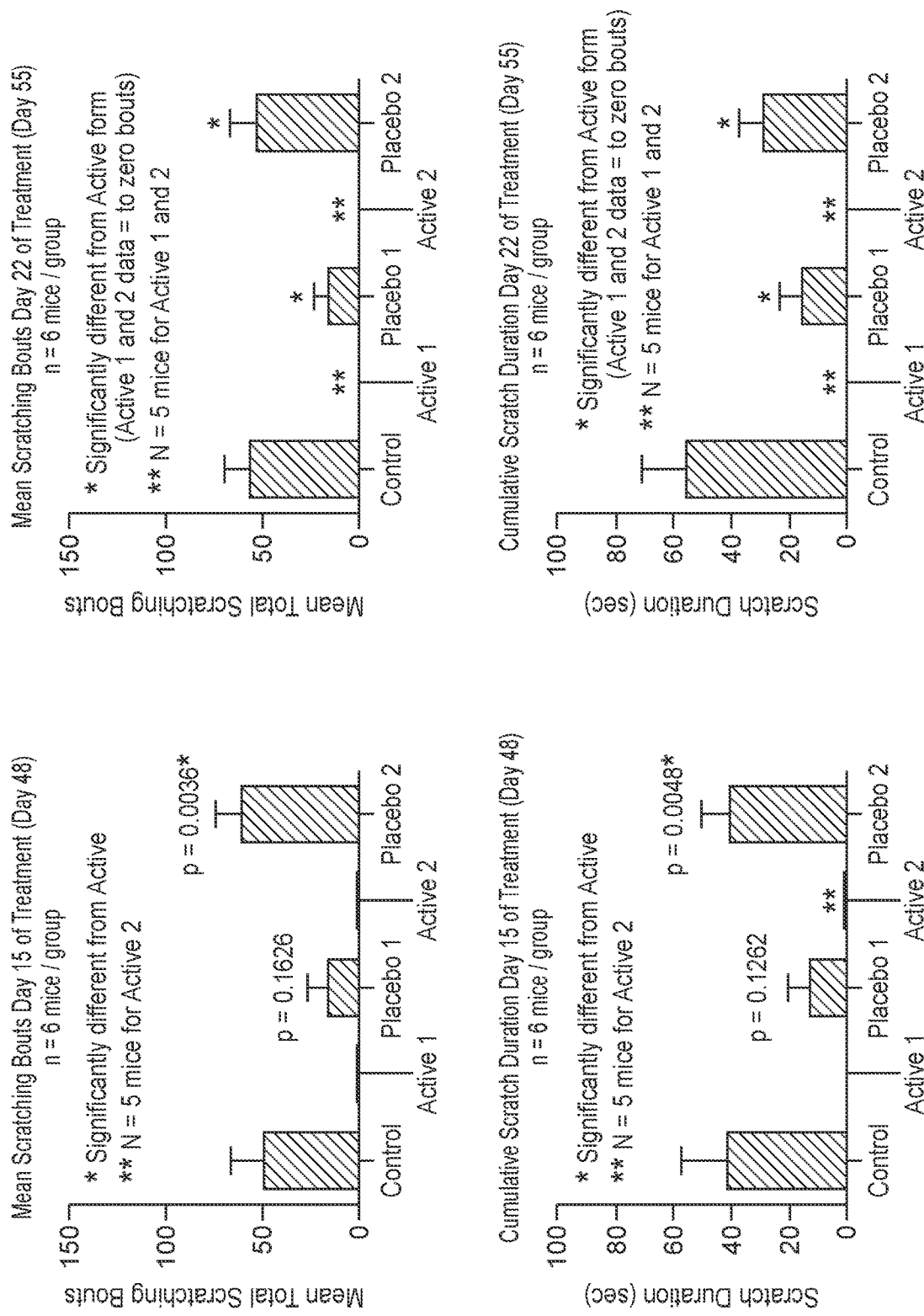
FIG. 4 depicts the mean scratching bouts and cumulative scratching duration exhibited by mice at days 48 and 55 applied with: 1) placebo (no naloxone active agent); 5 or 2) a topical composition having naloxone free base.

FIG. 3 depicts the mean scratching bouts and cumulative scratching duration exhibited by mice at days 34 and 41 and FIG. 4 depicts the mean scratching bouts and cumulative scratching duration exhibited by mice at days 48 and 55 applied with: 1) placebo (no naloxone active agent); 5 or 2) a topical composition having naloxone free base. The results also compare the scratching behavior of mice applied with topical compositions having either a hydrophilic delivery vehicle containing a polyethylene glycol or in the presence of a hydrophobic delivery vehicle (a petrolatum).

Figure 5:
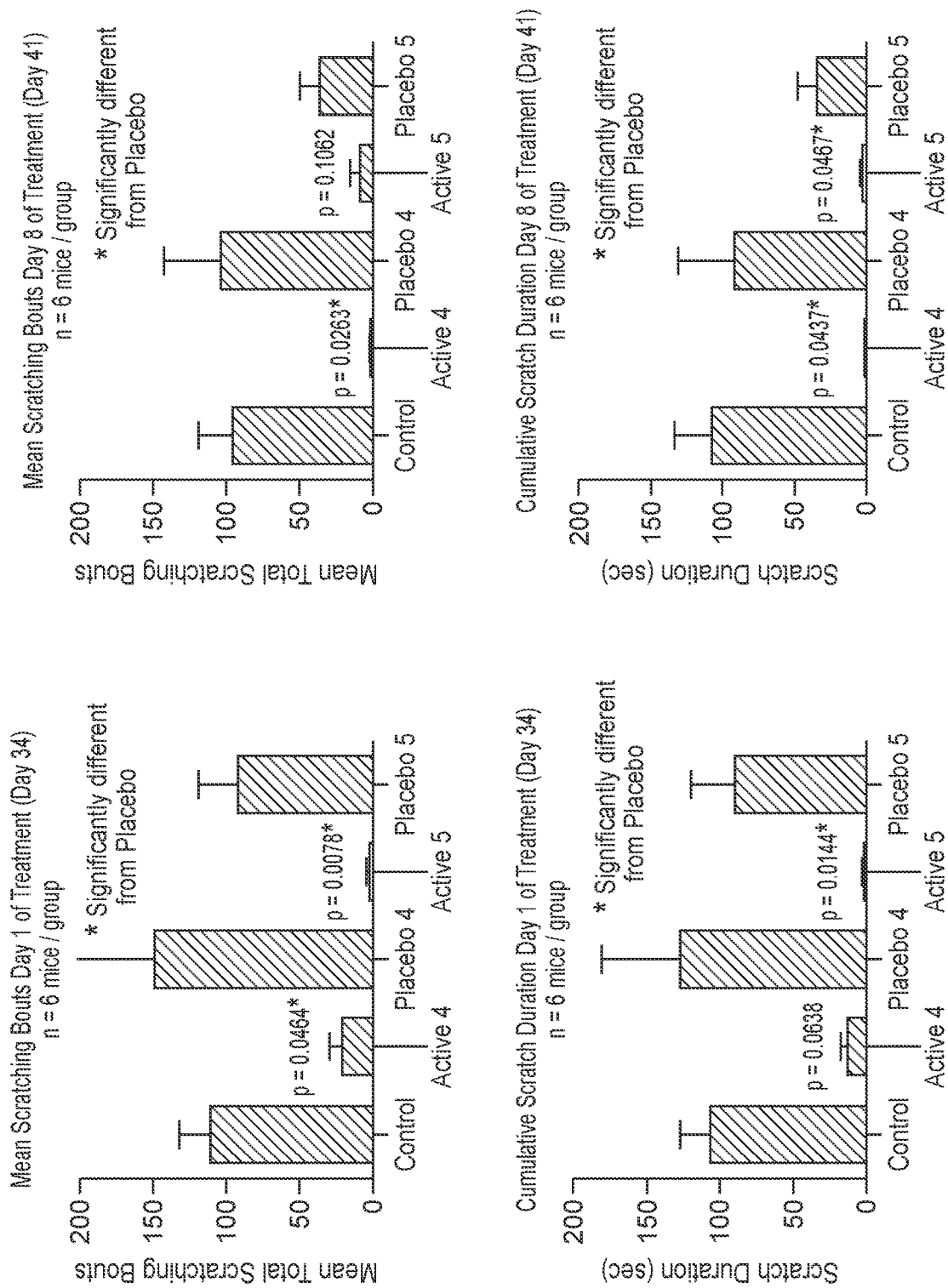
FIG. 5 depicts the mean scratching bouts and cumulative scratching duration exhibited by mice at days 34 and 41 applied with: 1) placebo (no naloxone active agent); or 2) a topical composition having naloxone HCl.
Figure 6:
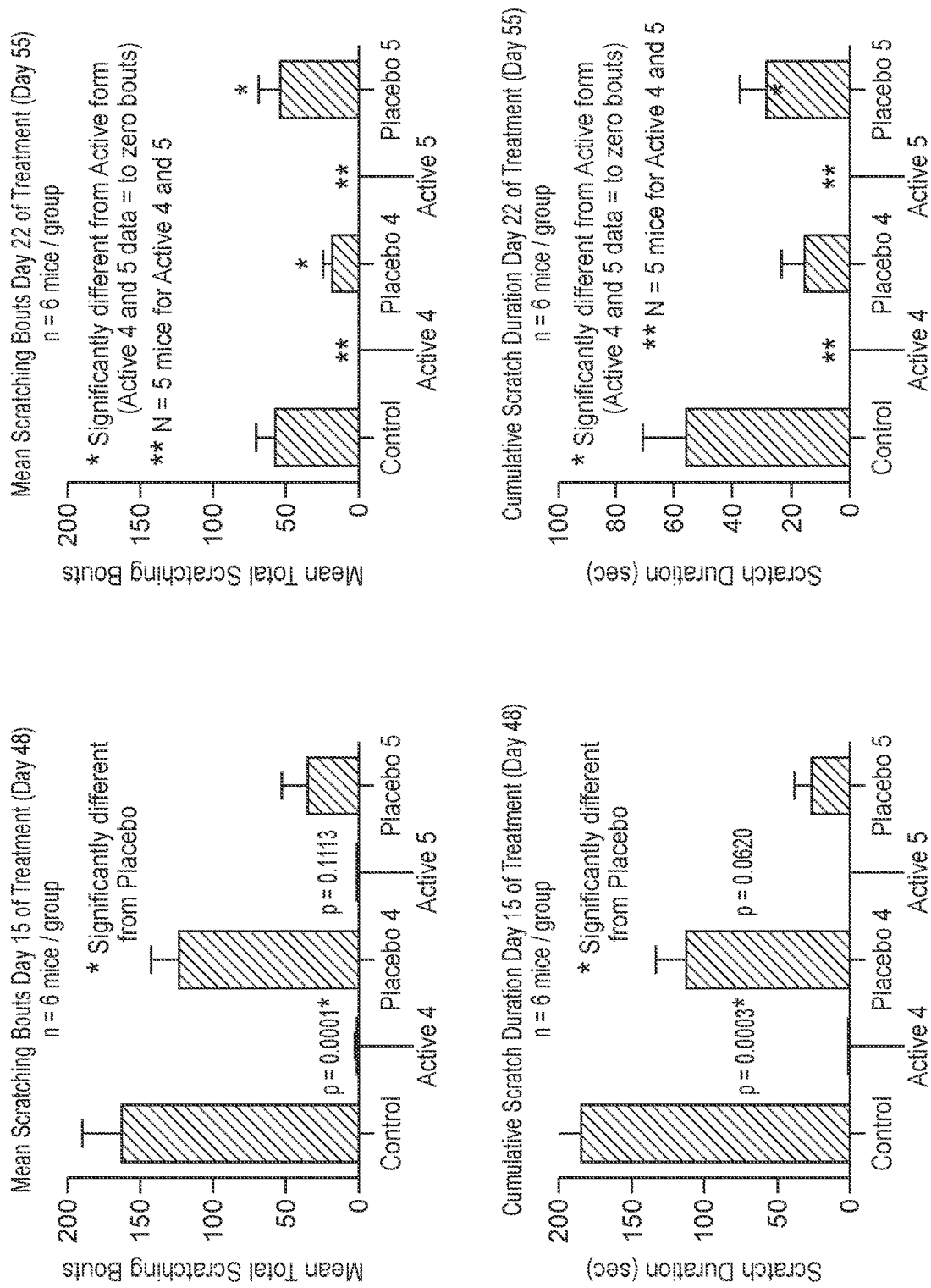
FIG. 6 depicts the mean scratching bouts and cumulative scratch duration exhibited by mice at days 48 and 55 applied with: 1) placebo (no naloxone active agent); or 2) a topical composition having naloxone HCl.

FIG. 5 depicts the mean scratching bouts and cumulative scratching duration exhibited by mice at days 34 and 41 and FIG. 6 depicts the mean scratching bouts and cumulative scratch duration exhibited by mice at days 48 and 55 applied with: 1) placebo (no naloxone active agent); or 2) a topical composition having naloxone HCl. The results also compare the scratching behavior of mice applied with topical compositions having either a hydrophilic delivery vehicle containing a polyethylene glycol or in the presence of a hydrophobic delivery vehicle (a petrolatum).

As shown in FIGS. 3-6, both the mean scratching bouts and the cumulative scratching duration were decreased by local delivery of either naloxone free base or naloxone HCl. In addition, the mean scratching bouts and cumulative scratching duration were significantly decreased by application of topical compositions having a naloxone active agent and only a hydrophilic delivery vehicle (polyethylene glycol).

Figure 7A:
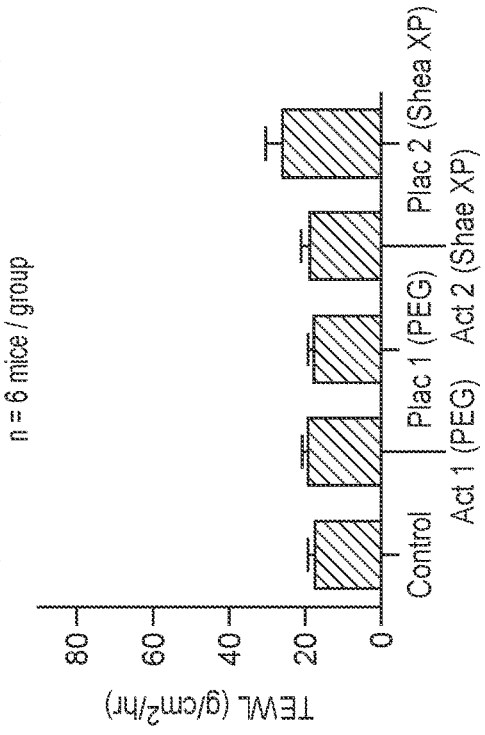
FIGS. 7A-7C depict the trans-epidermal water loss exhibited at Day 34, Day 48 and Day 55 for placebo (no naloxone active agent) compositions and topical compositions having a naloxone free base.
Figure 7C:
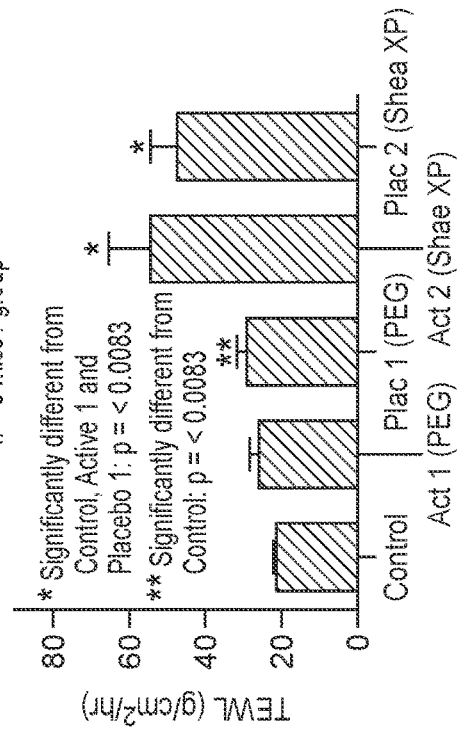
Figure 7B:
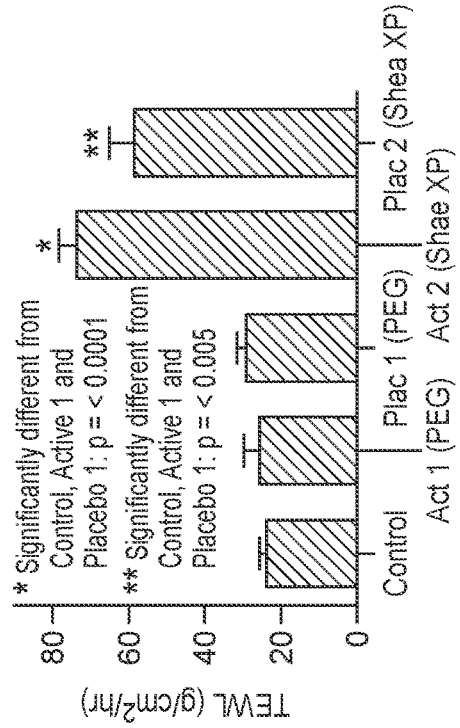

FIGS. 7A-7C depict the trans-epidermal water loss exhibited at Day 34, Day 48 and Day 55 for placebo (no naloxone active agent) compositions and topical compositions having a naloxone free base. As shown in FIGS. 7A-7C, a greater trans-epidermal water loss was exhibited by compositions containing a hydrophobic delivery vehicle, which is atypical since hydrophobic delivery 5 vehicles such as petrolatums generally reduce water loss.

Figure 8A:
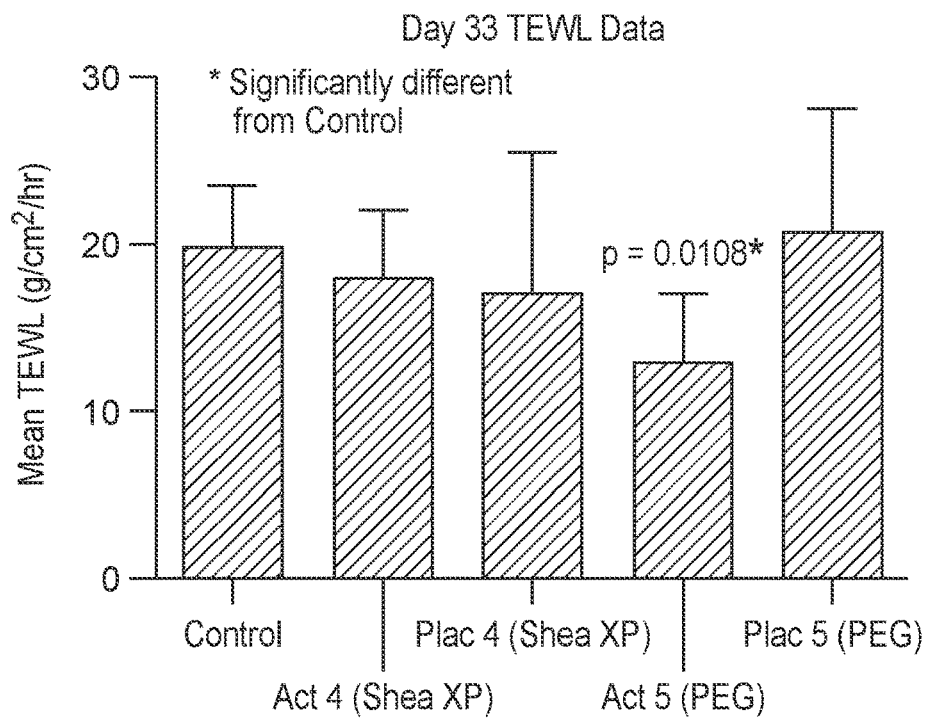
FIGS. 8A-8B depict the trans-epidermal water loss exhibited at Day 33 and Day 55 for placebo (no naloxone active agent) compositions and topical compositions having a naloxone HCl.
Figure 8B:
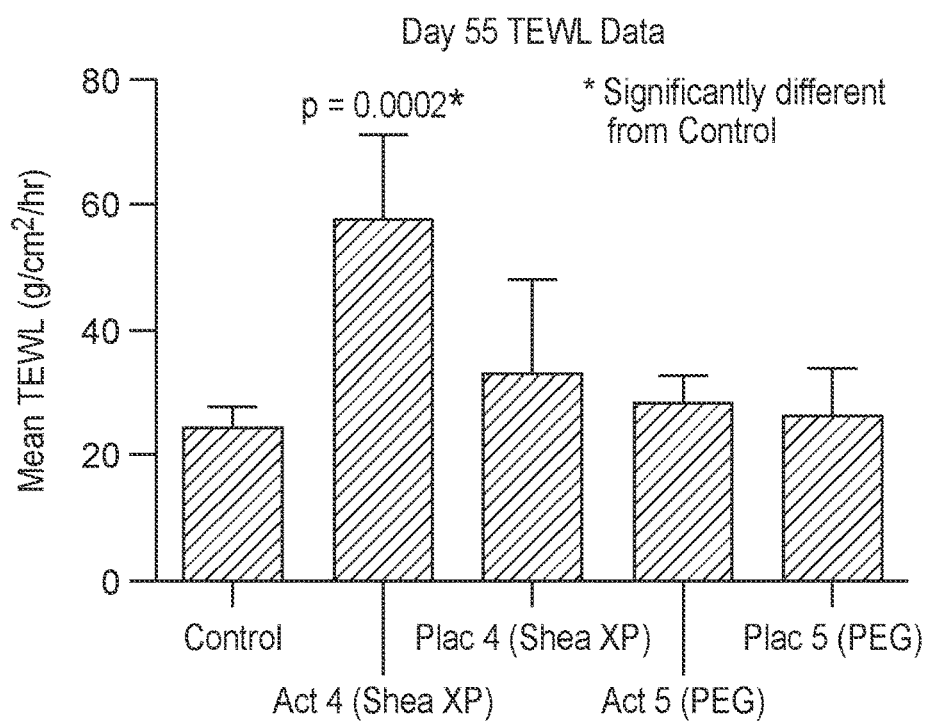

FIGS. 8A-8B depict the trans-epidermal water loss exhibited at Day 33 and Day 55 for placebo (no naloxone active agent) compositions and topical compositions having a naloxone HCl. Like the compositions with naloxone free base, a greater trans-epidermal water loss was exhibited by compositions containing a hydrophobic delivery vehicle than that exhibited by compositions with only the polyethylene glycol containing hydrophilic delivery vehicle.

Figure 10B:
FIGS. 10A-10B depict example photographs of the skin of mice applied with placebo (no naloxone active agent) compositions and topical compositions having naloxone HCl and only a polyethylene glycol containing hydrophilic delivery vehicle.
Figure 10A:

FIGS. 9A-9B depict example photographs of the skin of mice applied with placebo (no naloxone active agent) compositions and topical compositions having naloxone free base and hydrophobic delivery vehicle. FIGS. 10A-10B depict example photographs of the skin of mice applied with placebo (no naloxone active agent) compositions and topical compositions having naloxone HCl and only a polyethylene glycol containing hydrophilic delivery vehicle. A comparison of FIGS. 9A-9B with FIGS. 10A-10B demonstrates that the skin of mice subjects applied with topical compositions that only include a hydrophilic delivery vehicle exhibit less irritation, redness and damage due to scratching bouts.

All of the tested naloxone topical compositions demonstrated antipruritic effect in the hairless mouse model. Compared to the placebo group, a significant reduction in scratching behavior was seen for Naloxone base+PEG (Days 41 & 55) and Naloxone base+Shea XP (Days 48 & 55). Compared to the placebo group, a significant reduction in scratching behavior was seen for Naloxone HCl+PEG (Days 34 & 55) and Naloxone HCl+Shea XP (Days 34, 41, 48 & 55). Trans-epidermal water loss, however, was significantly higher for formulations containing Shea XP compared to PEG formulations with either Naloxone base or Naloxone HCl.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A storage stable non-aqueous topical composition comprising:
    naloxone free base, and
    a non-aqueous vehicle comprising a first polyethylene glycol having an average molecular weight of 600 g/mol or less, and a second polyethylene glycol having an average molecular weight of 1000 g/mol or greater,
    wherein the composition is substantially free of naloxone N-oxide and is formulated to deliver naloxone through a skin surface of the subject.

2. The storage stable non-aqueous topical composition according to claim 1, wherein naloxone free base is present in the composition in an amount of 0.05 to 10% by weight.

3. The storage stable non-aqueous topical composition according to claim 2, wherein the naloxone free base is present in the composition in an amount of 0.1 to 5% by weight.

4. The storage stable non-aqueous topical composition according to claim 1, wherein the second polyethylene glycol has an average molecular weight of 1350 g/mol or higher.

5. The storage stable non-aqueous topical composition according to claim 1, wherein the first polyethylene glycol has an average molecular weight of 300 to 400 g/mol.

6. The storage table non-aqueous topical composition according to claim 4, wherein the second polyethylene glycol has an average molecular weight of 1400 to 1500 g/mol.

7. The storage stable non-aqueous topical composition according to claim 5, wherein the composition comprises from 20 to 90% by weight of the first polyethylene glycol.

8. The storage stable non-aqueous topical composition according to claim 7, wherein the composition comprises more of the first polyethylene glycol than the second polyethylene glycol.

9. The storage stable non-aqueous topical composition according to claim 7, wherein the composition comprises from 20 to 50% by weight of the second polyethylene glycol.

10. The storage stable non-aqueous topical composition according to claim 1, wherein at least the first polyethylene glycol component comprises 20 ppm peroxides or less at the time the composition is prepared.

11. The storage stable non-aqueous topical composition according to claim 1, wherein the composition comprises:
    1% by weight naloxone free base,
    20 to 90% by weight of the first polyethylene glycol, wherein the first polyethylene glycol has an average molecular weight of 300 to 400 g/mol, and
    20 to 50% by weight of the second polyethylene glycol, wherein the second polyethylene glycol has an average molecular weight of 1400 to 1500 g/mol.

12. The storage stable non-aqueous topical composition according to claim 1, wherein the composition is substantially free of one or more additional impurities.

13. The storage stable non-aqueous topical composition according to claim 12, wherein the one or more additional impurities are selected from RRT0.32, RRT0.43, RRT0.82, RRT0.86, and RRT2.63.

14. The storage stable non-aqueous topical composition according to claim 1, wherein the composition comprises one or more anti-oxidants.

15. The storage stable non-aqueous topical composition according to claim 14, wherein the one or more anti-oxidants are selected from BHT and propyl gallate.

16. The storage stable non-aqueous topical composition according to claim 1, wherein the composition is a cream, gel, lotion or ointment.

17. A kit comprising:
    a topical composition according to claim 1; and
    a dispensing device.

* * * * *